(12) United States Patent
Mermelshtein et al.

(10) Patent No.: US 12,123,504 B2
(45) Date of Patent: *Oct. 22, 2024

(54) CLOSED STOPCOCK

(71) Applicant: ELCAM MEDICAL AGRICULTURAL COOPERATIVE ASSOCIATION LTD, Merom Hagalil (IL)

(72) Inventors: Gilad Mermelshtein, Misgav-Am (IL); Hilel Yeshayahu, Tzefat (IL); Ilan Shopen, Tzefat (IL)

(73) Assignee: ELCAM MEDICAL AGRICULTURAL COOPERATIVE ASSOCIATION LTD, Merom Hagalil (IL)

( * ) Notice: Subject to any disclaimer, the term of this patent is extended or adjusted under 35 U.S.C. 154(b) by 172 days.

This patent is subject to a terminal disclaimer.

(21) Appl. No.: 17/679,534

(22) Filed: Feb. 24, 2022

(65) Prior Publication Data

US 2022/0268366 A1 Aug. 25, 2022

Related U.S. Application Data

(63) Continuation of application No. 16/611,976, filed as application No. PCT/IL2018/050610 on Jun. 5, 2018, now Pat. No. 11,306,832.

(Continued)

(51) Int. Cl.
*F16K 11/083* (2006.01)
*A61B 5/15* (2006.01)
(Continued)

(52) U.S. Cl.
CPC .... *F16K 11/0833* (2013.01); *A61B 5/150992* (2013.01); *A61M 5/16877* (2013.01);
(Continued)

(58) Field of Classification Search
None
See application file for complete search history.

(56) References Cited

U.S. PATENT DOCUMENTS

| 2,868,176 A | 1/1959 | Bennett |
| 3,185,179 A | 5/1965 | Harautuneian |

(Continued)

FOREIGN PATENT DOCUMENTS

| DE | 10-2007-003690 A1 | 8/2008 |
| DE | 10 2015 205 517 A1 | 9/2016 |

(Continued)

OTHER PUBLICATIONS

An Office Action dated Sep. 13, 2012 which issued during the prosecution of Canadian Patent Application No. 2,578,989.

(Continued)

*Primary Examiner* — Matthew W Jellett
(74) *Attorney, Agent, or Firm* — Sughrue Mion, PLLC

(57) ABSTRACT

A stopcock, comprising a housing element defining a central bore and at least first, second and third ports; and a handle element which is selectably positionable relative to the housing element; at least one of the housing element and the handle element defining: a first fluid flow passageway communicating between two of the at least first, second and third ports; a second fluid flow passageway communicating between at least two of the at least first, second and third ports, and a fluid flow guide associated with the second fluid flow passageway, the fluid flow guide extending radially towards an inner facing wall of the central bore.

17 Claims, 28 Drawing Sheets

Related U.S. Application Data

(60) Provisional application No. 62/523,252, filed on Jun. 22, 2017.

(51) Int. Cl.
*A61M 5/168* (2006.01)
*A61M 39/22* (2006.01)
*F16K 31/60* (2006.01)

(52) U.S. Cl.
CPC ......... *A61M 39/223* (2013.01); *F16K 31/602* (2013.01); *A61M 2039/229* (2013.01)

(56) References Cited

U.S. PATENT DOCUMENTS

| | | | |
|---|---|---|---|
| 3,362,400 A | 1/1968 | De Bella | |
| 3,721,265 A * | 3/1973 | Hoffland | F16K 11/08 251/312 |
| 3,780,736 A | 12/1973 | Chen | |
| 3,834,372 A | 9/1974 | Turney | |
| 3,927,693 A | 12/1975 | Johnston | |
| 4,146,055 A | 3/1979 | Ryder et al. | |
| 4,207,923 A * | 6/1980 | Giurtino | F16K 11/0853 251/181 |
| 4,314,586 A * | 2/1982 | Folkman | F16K 11/0853 251/368 |
| 4,397,335 A | 8/1983 | Doblar et al. | |
| 4,608,996 A | 9/1986 | Brown | |
| 4,654,027 A | 3/1987 | Dragan et al. | |
| 4,697,797 A | 10/1987 | Gold | |
| 4,967,797 A | 11/1990 | Manska | |
| 5,002,066 A | 3/1991 | Simpson et al. | |
| 5,074,334 A | 12/1991 | Onodera | |
| 5,105,853 A | 4/1992 | Lie | |
| 5,135,026 A | 8/1992 | Manska | |
| 5,340,634 A | 8/1994 | Adams | |
| 5,466,228 A | 11/1995 | Evans | |
| 5,549,651 A | 8/1996 | Lynn | |
| 5,578,016 A | 11/1996 | Zinger | |
| 5,817,068 A | 10/1998 | Urrutia | |
| 6,036,171 A | 3/2000 | Weinheimer et al. | |
| 6,089,541 A | 7/2000 | Weinheimer et al. | |
| 6,238,372 B1 | 5/2001 | Zinger et al. | |
| RE37,357 E | 9/2001 | Lynn | |
| 6,651,956 B2 | 11/2003 | Miller | |
| 6,780,736 B1 | 8/2004 | Holmes et al. | |
| 6,864,372 B2 | 3/2005 | Kano et al. | |
| 7,186,236 B2 | 3/2007 | Gibson et al. | |
| 7,232,428 B1 | 6/2007 | Inukai et al. | |
| 7,470,261 B2 | 12/2008 | Lynn | |
| 7,520,489 B2 | 4/2009 | Ruschke et al. | |
| 7,695,445 B2 | 4/2010 | Yuki | |
| 7,984,730 B2 | 7/2011 | Ziv et al. | |
| 8,584,701 B2 | 11/2013 | Duncan | |
| 2004/0210162 A1 | 10/2004 | Wyatt et al. | |
| 2010/0305507 A1 | 12/2010 | Duncan | |
| 2013/0060205 A1 | 3/2013 | Mansour et al. | |
| 2014/0018746 A1 | 1/2014 | Ueda et al. | |
| 2017/0016381 A1 | 1/2017 | Yumisashi et al. | |
| 2017/0152957 A1 | 6/2017 | Roche et al. | |
| 2018/0050187 A1 | 2/2018 | Kunschak et al. | |

FOREIGN PATENT DOCUMENTS

| | | |
|---|---|---|
| EP | 1 234 596 B1 | 1/2007 |
| EP | 1 426 604 B1 | 5/2010 |
| GB | 142041 A | 4/1920 |
| JP | 11-342209 A | 12/1999 |
| JP | 2002-153562 A | 5/2002 |
| JP | 2003-159336 A | 6/2003 |
| JP | 5092147 B2 | 12/2012 |
| JP | 2013-000913 A | 1/2013 |
| JP | 5415073 B2 | 2/2014 |
| WO | 2006/025054 A2 | 3/2006 |
| WO | 2007/033319 A1 | 3/2007 |

OTHER PUBLICATIONS

An Office Action dated May 8, 2012, which issued during the prosecution of European Patent Application No. 05775471.5.

An Office Action dated Oct. 31, 2014, which issued during the prosecution of European Patent Application No. 05775471.5.

An English Translation of an Office Action dated Feb. 5, 2013, which issued during the prosecution of Japanese Application No. 2011-202066.

* cited by examiner

CLOSED STOPCOCK

REFERENCE TO RELATED APPLICATIONS

This is a Continuation application of U.S. application Ser. No. 16/611,976, filed Nov. 8, 2019, which is a National Stage of International Application No. PCT/IL2018/050610, filed Jun. 5, 2018, claiming priority based on U.S. Provisional Patent Application 62/523,252, filed Jun. 22, 2017, the disclosures of which are incorporated by reference in their entirety

FIELD OF THE INVENTION

The present invention relates to stopcocks generally, and more specifically to swabbable stopcocks.

BACKGROUND OF THE INVENTION

Various fluid flow regulators, such as stopcocks, are known in the art. Closed stopcocks typically have a luer activated valve incorporated within one of the stopcock ports for convenient engagement of a medical instrument with the stopcock.

SUMMARY OF THE INVENTION

The present invention seeks to provide an improved closed stopcock.

There is thus provided in accordance with an embodiment of the present invention that a stopcock comprising a housing element defining a central bore and at least first, second and third ports; and a handle element which is selectably positionable in one of a plurality of mutual positions relative to the housing element. At least one of the housing element and the handle element defining: at least one fluid flow passageway communicating between two of the at least first, second and third ports; and a fluid flow guide associated with the at least one fluid flow passageway, the fluid flow guide extending radially towards an inner facing wall of the central bore.

Preferably, the at least one fluid flow passageway includes a first fluid flow passageway communicating between two of the at least first, second and third ports; and a second fluid flow passageway communicating between at least two of the at least first, second and third ports, and wherein the fluid flow guide is associated with the second fluid flow passageway.

There is thus further provided in accordance with an embodiment of the present invention that a stopcock comprising a housing element defining a central bore and at least first, second and third ports; and a handle element which is selectably positionable relative to the housing element; at least one of the housing element and the handle element defining: a first fluid flow passageway communicating between two of the at least first, second and third ports; a second fluid flow passageway communicating between at least two of the at least first, second and third ports, and a fluid flow guide associated with the second fluid flow passageway, the fluid flow guide extending radially towards an inner facing wall of the central bore.

Preferably, the second fluid flow passageway being configured for enabling flushing an internal volume of at least one of the first, second and third ports by a fluid flow which does not flow entirely through the port whose internal volume is being flushed, and the first fluid flow passageway being configured for increasing a fluid flow rate between two of the at least first, second and third ports.

Further preferably, the fluid flow guide partially bifurcates the second fluid flow passageway.

In accordance with an embodiment of the present invention, the fluid flow guide comprising an outward facing edge which sealingly engages the inner facing wall of the central bore, and when the outward facing edge of the fluid flow guide is not located opposite any of the first, second and third ports, flow of liquid through the second fluid flow passageway is prevented and flow of liquid through the first fluid flow passageway is allowed.

Alternatively, the fluid flow guide comprising an outward facing edge which is slightly spaced from the inner facing wall of the central bore, and when the outward facing edge of the fluid flow guide is not located opposite any of the first, second and third ports, minimal flow of liquid through the second fluid flow passageway is allowed and flow of liquid through the first fluid flow passageway is allowed.

Preferably, the handle element and the housing element being arrangeable in multiple mutual positions. Further preferably, the fluid flow guide and the second fluid flow passageway being configured for enabling flushing an internal volume of at least one of said first, second and third ports by a fluid flow which does not flow entirely through the port whose internal volume is being flushed when the housing element and the handle element are in at least one of the multiple mutual positions.

Still further preferably, the first fluid flow passageway and the second fluid flow passageway are operative simultaneously in at least one of the multiple mutual positions. Yet further preferably, the stopcock also comprising a second fluid flow guide extending radially and partially bifurcating one of the at least one of the first, second and third ports, the second fluid flow guide being associated with at least one of the first fluid flow passageway and said second fluid flow passageway.

In accordance with an embodiment of the present invention, the stopcock also comprising at least one valve, which is associated with at least one of the first, second and third ports. Preferably, the valve includes an elastomeric element, and wherein at least one of the first fluid flow passageway and the second fluid flow passageway is configured for providing a fluid flow which is sealed from the elastomeric element when the housing element and the handle element are in another one of the mutual positions.

Further preferably, both the first fluid flow passageway and the second fluid flow passageway are defined by a shaft portion of the handle element. Still further preferably, the first fluid flow passageway is defined by at least one side-to-side extending bore formed within the shaft portion of the handle element. Yet further preferably, the at least one side-to-side extending bore has a semi-circular cross-section.

In accordance with an embodiment of the present invention, the handle element has a partially peripherally-extending recess, selectably defining the second fluid flow passageway, the fluid flow guide extending radially and partially bifurcating the recess.

Preferably, the at least one side-to-side extending bore is spaced from the recess. Alternatively, the at least one side-to-side extending bore is interconnected with the recess.

Preferably, the fluid flow rate is increased by at least 25%. Further preferably, the fluid flow rate is at least 500 ml/min.

In accordance with an embodiment of the present invention, the fluid flow guide has a flat wall extending towards an inner wall of the central bore and a concave wall portion formed on each side of the flat wall. Preferably, the concave wall portion extends outwardly from the flat wall along a relatively minor longitudinal extent of the side-to-side extending bore.

Alternatively, the fluid flow guide has an inclined wall portion and a concave wall portion. Preferably, both the inclined wall portion and the concave wall portion extend to the vicinity of the side-to-side extending bore and along a relatively minor longitudinal extent of the side-to-side extending bore.

Further alternatively, the fluid flow guide has a concave wall portion and a convex wall portion connected with a straight wall portion. Preferably, both the concave wall portion and the convex wall portion extend to the vicinity of the side-to-side extending bore and along a relatively minor longitudinal extent of the side-to-side extending bore.

Still further alternatively, the fluid flow guide has two concave wall portions. Preferably, both the concave wall portions extend to the vicinity of the side-to-side extending bore and along a relatively major longitudinal extent of the side-to-side extending bore.

Preferably, the first fluid flow passageway is fluidly connected with the second fluid flow passageway in at least one of the mutual positions. Alternatively, the first fluid flow passageway is fluidly isolated from the second fluid flow passageway in at least one of the mutual positions.

In accordance with an embodiment of the present invention, a stopcock comprising a housing element defining a central bore and at least first, second and third ports, and a handle element, which is selectably positionable relative to the housing element, the housing element and the handle element being arrangeable in multiple mutual positions, at least one of the housing element and the handle element defining a first fluid flow passageway communicating between two of said at least first, second and third ports, and a second fluid flow passageway communicating between at least two of the at least first, second and third ports, selection of the ports being in accordance with a relative position of the handle element relative to the housing element; the first fluid flow passageway including a side-to-side extending bore extending through the handle, and the second fluid flow passageway including a fluid flow guide.

Preferably, the fluid flow guide extends radially towards an inner facing wall of the central bore and partially bifurcates the second fluid flow passageway. Further preferably, the first fluid flow passageway and the second fluid flow passageway are operative simultaneously in at least one of the multiple mutual positions.

Still further preferably, the stopcock also comprising a second fluid flow guide extending radially and partially bifurcating one of the at least one of the first, second and third ports, the second fluid flow guide being associated with at least one of the first fluid flow passageway and the second fluid flow passageway.

Yet further preferably, the second fluid flow passageway being configured for enabling flushing an internal volume of at least one of the first, second and third ports by a fluid flow which does not flow entirely through the port whose internal volume is being flushed, and the first fluid flow passageway being configured for increasing a fluid flow rate between two of the at least first, second and third ports.

In accordance with an embodiment of the present invention, the fluid flow guide comprising an outward facing edge which sealingly engages an inner facing wall of the central bore, and when the outward facing edge of the fluid flow guide is not located opposite any of the first, second and third ports, flow of liquid through the second fluid flow passageway is prevented and flow of liquid through the first fluid flow passageway is allowed.

Alternatively, the fluid flow guide comprising an outward facing edge which is slightly spaced from an inner facing wall of the central bore, and when the outward facing edge of the fluid flow guide is not located opposite any of the first, second and third ports, minimal flow of liquid through the second fluid flow passageway is allowed and flow of liquid through the first fluid flow passageway is allowed.

In accordance with an embodiment of the present invention, the stopcock also comprising at least one valve, which is associated with at least one of the first, second and third ports. Preferably, the valve includes an elastomeric element, and wherein at least one of the first fluid flow passageway and the second fluid flow passageway is configured for providing a fluid flow which is sealed from the elastomeric element when the housing element and the handle element are in another one of the mutual positions.

Further preferably, both the first fluid flow passageway and the second fluid flow passageway are defined by a shaft portion of the handle element. Still further preferably, the at least one side-to-side extending bore has a semi-circular cross-section. Yet further preferably, the handle element has a partially peripherally-extending recess, selectably defining the second fluid flow passageway, the fluid flow guide extending radially and partially bifurcating the recess.

In accordance with an embodiment of the present invention, the at least one side-to-side extending bore is spaced from the recess. Alternatively, the at least one side-to-side extending bore is interconnected with the recess.

Preferably, the fluid flow rate is increased by at least 25%.

In accordance with an embodiment of the present invention, an arterial monitoring set comprising an arterial line adapted to be connected at a first end thereof to a source of liquid under pressure and at a second end thereof to an artery of a patient; a pressure transducer disposed along the arterial line for sensing liquid pressure therein; a stopcock disposed along the arterial line. The stopcock comprising: a housing element defining a central bore and at least first, second and third ports; a handle element which is selectably positionable in one of a plurality of mutual positions relative to said housing element; a first fluid flow passageway communicating between two of the at least first, second and third ports; a second fluid flow passageway communicating between at least two of the at least first, second and third ports. The first fluid flow passageway and the second fluid flow passageway being selectably defined by at least one of the housing element and the handle element; and wherein the second fluid flow passageway being configured for enabling flushing an internal volume of at least one of the first, second and third ports by a fluid flow which flows through the arterial line to the patient; and wherein the first fluid flow passageway being configured for increasing a fluid flow rate through the arterial line.

Preferably, the handle element and the housing element are arrangeable in multiple mutual positions and wherein the second fluid flow passageway is configured for enabling flushing the internal volume of at least one of the first, second and third ports when the housing element and the handle element are in at least one of the multiple mutual positions.

Further preferably, the stopcock also comprises at least one valve, which is associated with at least one of the first, second and third ports. Still further preferably, the valve includes an elastomeric element, and wherein the at least one of the first fluid flow passageway and the second fluid flow passageway is configured for providing a fluid flow which is sealed from the elastomeric element when the housing element and the handle are in another one of said mutual positions.

In accordance with an embodiment of the present invention, both the first fluid flow passageway and the second fluid flow passageway are defined by a shaft portion of the handle element.

Preferably, the stopcock also comprising a fluid flow guide associated with the second fluid flow passageway for enabling flushing of the internal volume of the at least one of the first, second and third ports when the housing element and the handle element are in the at least one of said mutual positions by the fluid flow which flows through the arterial line to the patient.

Further preferably, the fluid flow guide extends radially towards an inner facing wall of the central bore. Still further preferably, both the first fluid flow passageway and the second fluid flow passageway are defined by at least one side-to-side extending bore formed within the shaft portion of the handle element. Yet further preferably, the fluid flow guide extends radially and partially bifurcates the second fluid flow passageway.

In accordance with an embodiment of the present invention, the fluid flow guide comprising an outward facing edge which sealingly engages the inner facing wall of the central bore, and when the outward facing edge of the fluid flow guide is not located opposite any of the first, second and third ports, flow of liquid through the second fluid flow passageway is prevented and flow of liquid through the first fluid flow passageway is allowed.

Alternatively, the fluid flow guide comprising an outward facing edge which is slightly spaced from the inner facing wall of the central bore, and when the outward facing edge of the fluid flow guide is not located opposite any of the first, second and third ports, minimal flow of liquid through the second fluid flow passageway is allowed and flow of liquid through the first fluid flow passageway is allowed.

Preferably, at least one of the at least one ports is bifurcated by a second fluid flow guide. Further preferably, the first fluid flow passageway and the second fluid flow passageway are operative simultaneously in at least one of the multiple mutual positions.

Preferably, the first fluid flow passageway is fluidly connected with the second fluid flow passageway in at least one of the mutual positions. Alternatively, the first fluid flow passageway is fluidly isolated from the second fluid flow passageway in at least one of the mutual positions.

In accordance with an embodiment of the present invention, a method of providing fluid communication with the circulatory system of a patient comprising: providing a stopcock including: a housing element defining at least first, second and third ports; a handle element which is selectably positionable in one of a plurality of mutual positions relative to said housing element; a first fluid flow passageway communicating between two of the at least first, second and third ports; a second fluid flow passageway communicating between at least two of the at least first, second and third ports. The first fluid flow passageway and the second fluid flow passageway being selectably defined by at least one of the housing element and the handle element; at least one of the first fluid flow passageway and the second fluid flow passageway provides a flow of a first fluid through the stopcock in communication with the circulatory system of the patient when the handle element and the housing element are in a first mutual position; and at least one of the first fluid flow passageway and the second fluid flow passageway provides a flow of a second fluid through the stopcock in communication with the circulatory system of the patient when the handle element and the housing element are in a second mutual position, thereby flushing an internal volume of at least one of the first, second and third ports by the second fluid which does not flow entirely through the port whose internal volume is being flushed.

Preferably, the flow of the first fluid passes through the stopcock from the second port to the third port and the flow of the second fluid passes through the stopcock from the first port to the third port. Further preferably, the flow of the first fluid passes through the stopcock from the third port to the second port and the flow of the second fluid passes through the stopcock from the third port to the first port.

Still further preferably, the stopcock also comprises at least one valve, which is associated with at least one of the first, second and third ports. Yet further preferably, the valve includes an elastomeric element, and wherein at least the first passageway is configured for providing a fluid flow which is sealed from the elastomeric element when the housing element and the handle are in a third mutual position.

In accordance with an embodiment of the present invention, the first fluid flow passageway being configured for increasing fluid flow rate between two of the at least first, second and third ports. Preferably, the at least one of the at least one port is bifurcated by a second fluid flow guide. Further preferably, the first fluid flow passageway and the second fluid flow passageway are operative simultaneously in at least one of the multiple mutual positions.

In accordance with an embodiment of the present invention, the fluid flow passageway is fluidly connected with the second fluid flow passageway in at least one of the mutual positions. Alternatively, the first fluid flow passageway is fluidly isolated from the second fluid flow passageway in at least one of the mutual positions.

BRIEF DESCRIPTION OF THE DRAWINGS

The present invention will be understood and appreciated more fully from the following detailed description, taken in conjunction with the drawings in which.

DETAILED DESCRIPTION OF THE EMBODIMENTS OF INVENTION

Figure 1:
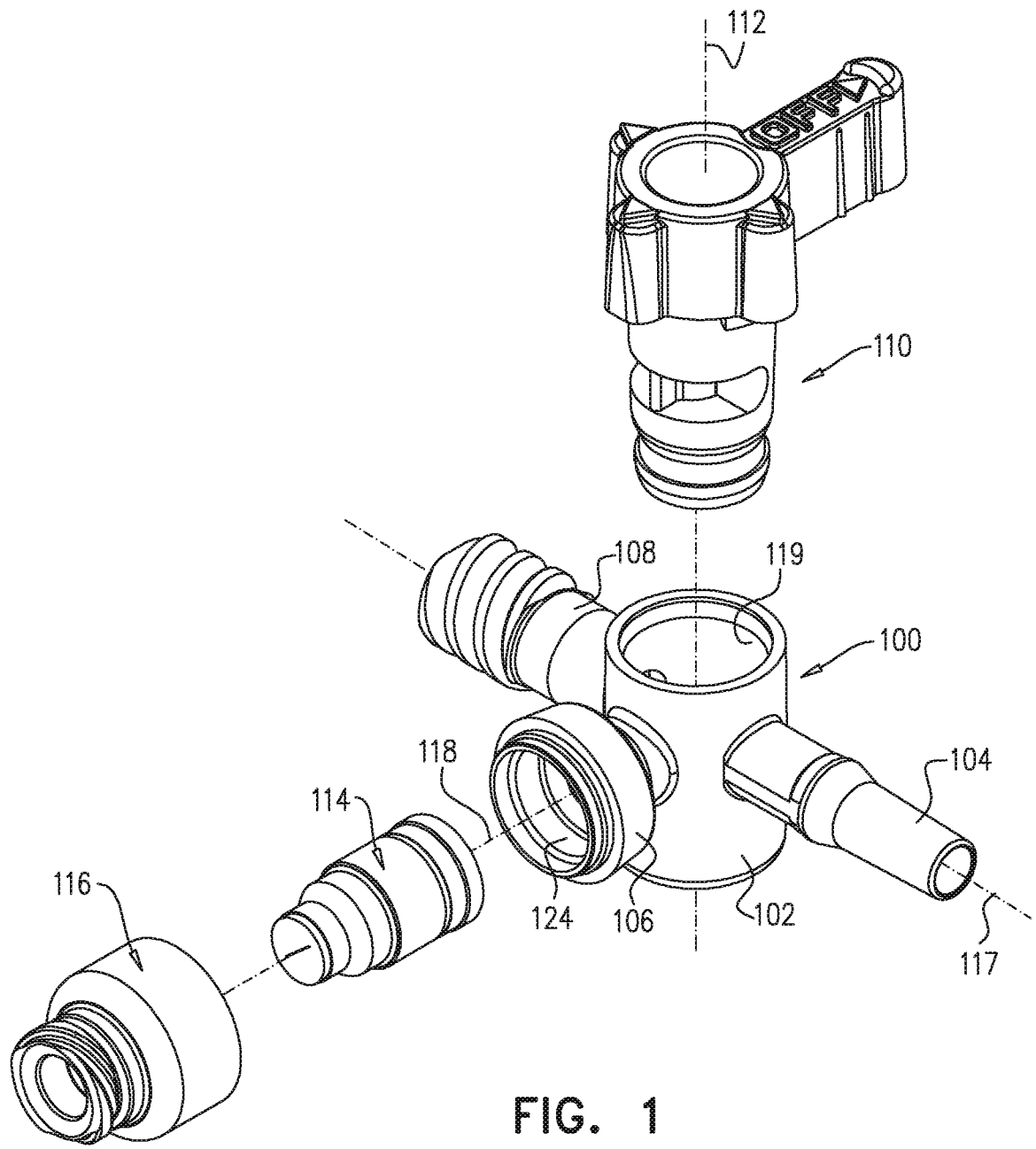
FIG. 1 is a simplified exploded view illustration of a stopcock constructed and operative in accordance with an embodiment of the present invention.

Reference is now made to FIG. 1, which is a simplified exploded view illustration of a stopcock constructed and operative in accordance with an embodiment of the present invention;

As seen in FIG. 1, the stopcock comprises a housing element 100 including a main tubular portion 102 and three side ports, designated by reference numerals 104, 106 and 108 respectively. A handle element 110 is arranged to be seated within main tubular portion 102 of housing element 100.

Figure 2A:
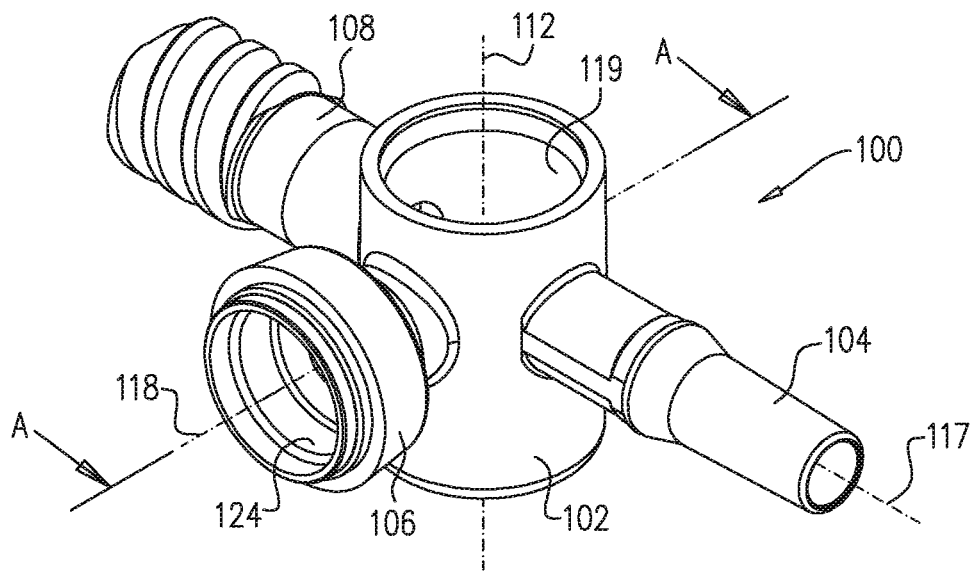
FIGS. 2A & 2B are simplified pictorial illustrations of a housing element, which forms part of the stopcock of FIG. 1 taken in two different directions.
Figure 2B:
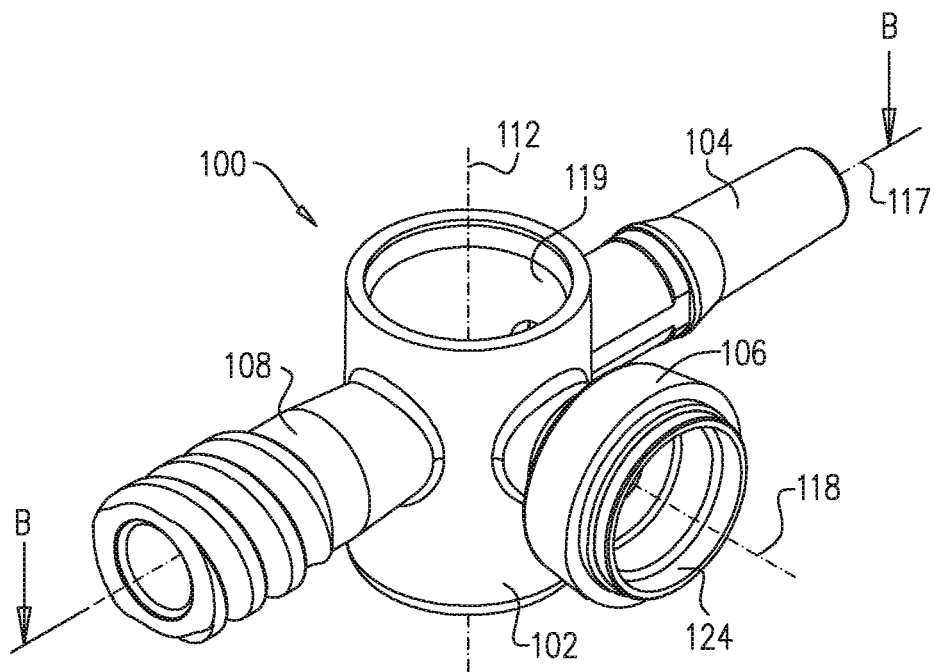
Figure 3A:
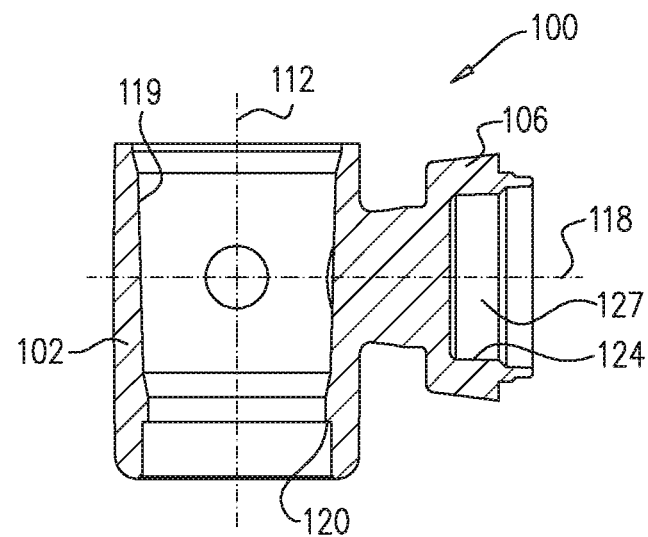
FIGS. 3A & 3B are sectional illustrations taken along section lines A-A and B-B in FIGS. 2A and 2B, respectively.
Figure 3B:
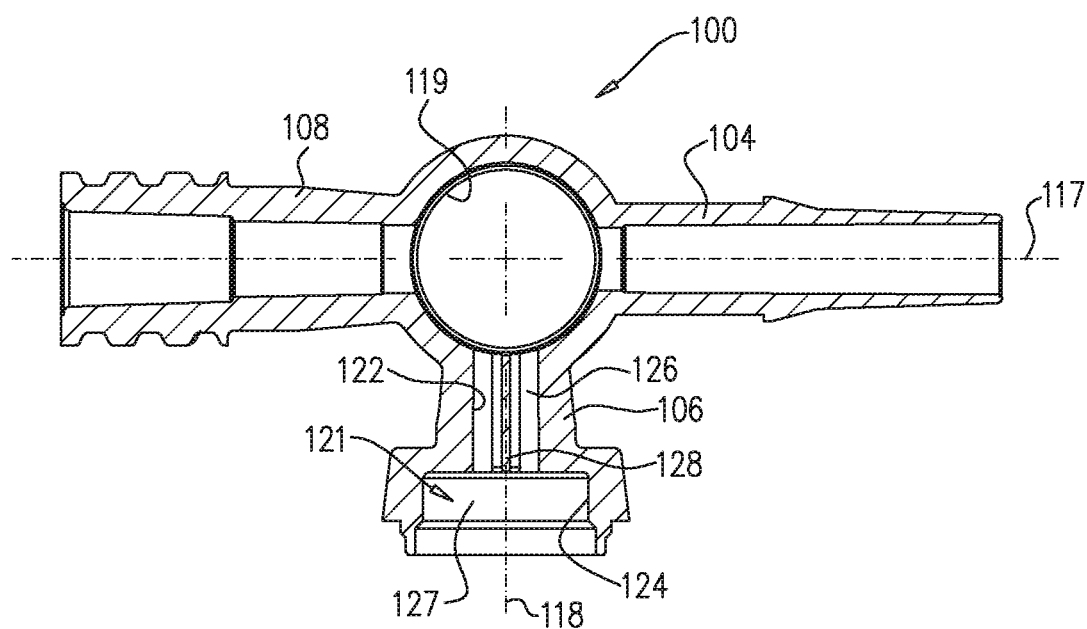
Figure 4A:
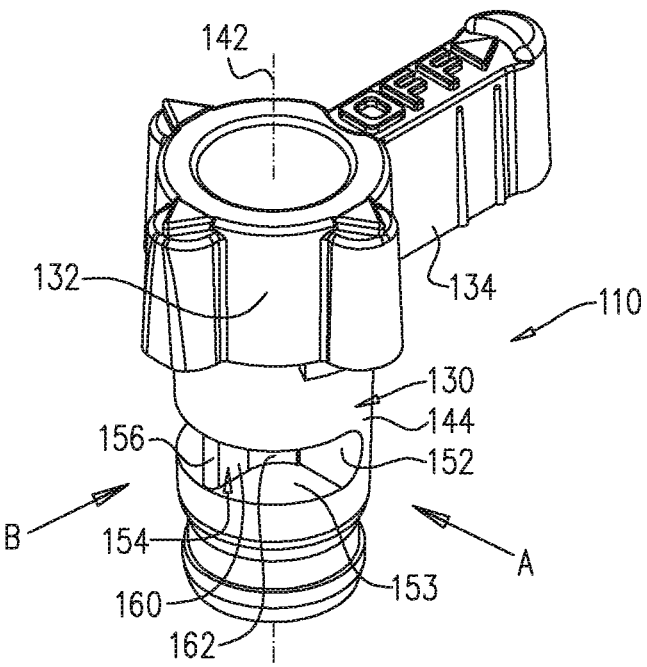
FIGS. 4A & 4B are simplified pictorial illustrations of a handle element, which forms part of the stopcock of FIG. 1 taken in two orientations.
Figure 4B:
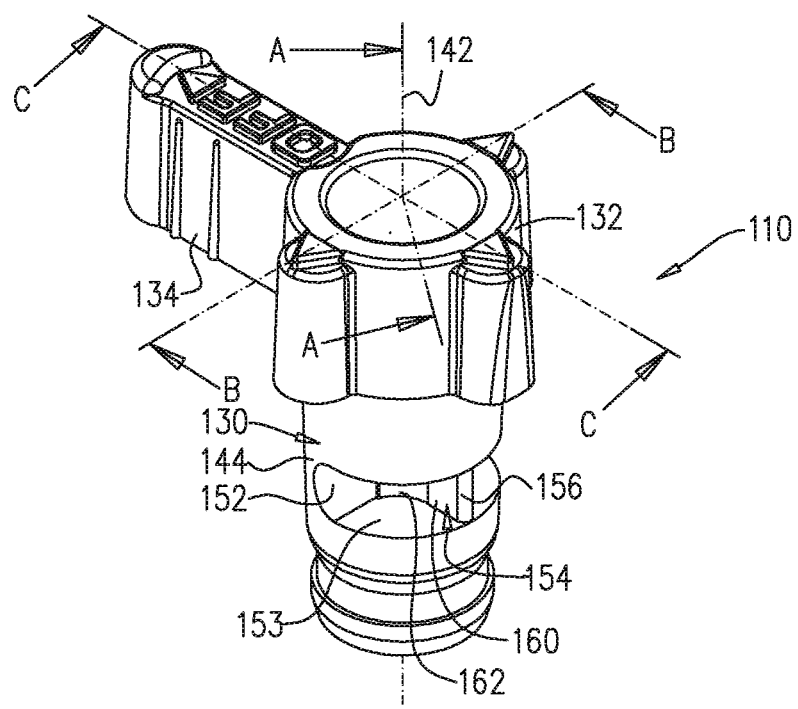
Figure 5A:
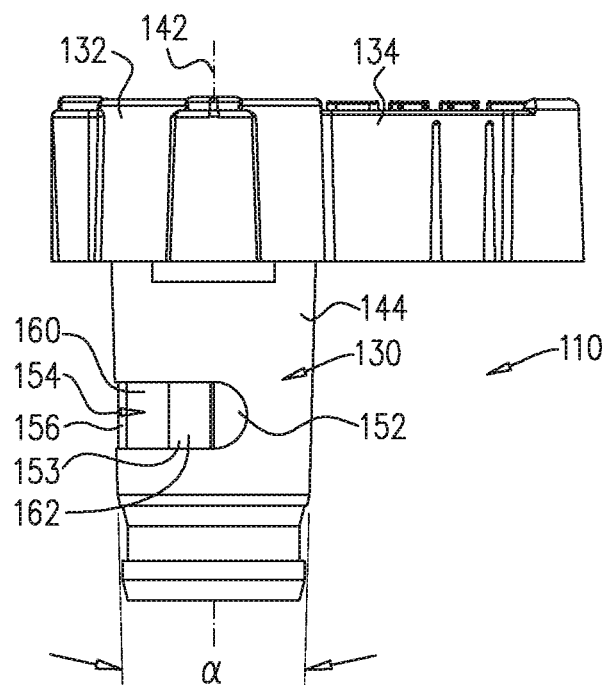
FIGS. 5A & 5B are simplified plan view illustrations of the handle element of FIGS. 4A & 4B taken along respective directions A and B in FIG. 4A.
Figure 5B:
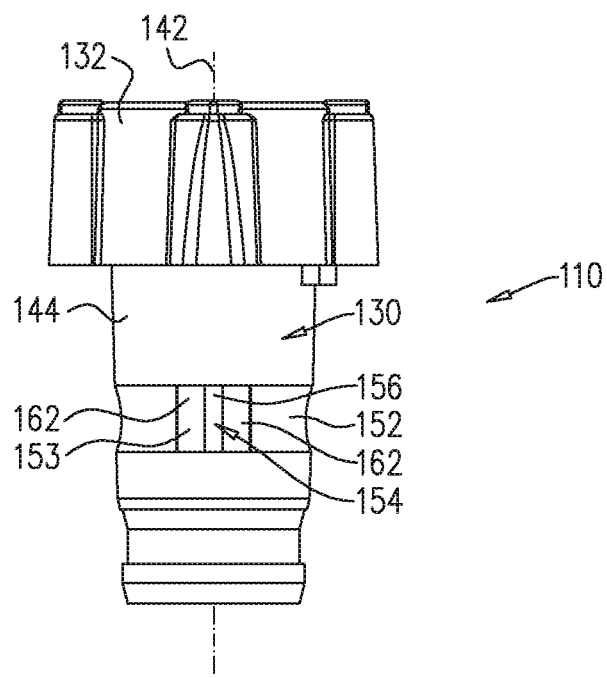

Reference is now made additionally to FIGS. 2A & 2B, which are simplified pictorial illustrations of the housing element 100 and to FIGS. 3A & 3B, which are sectional illustrations thereof.

As seen in FIGS. 1-3B, tubular portion 102 of housing element 100 is generally cylindrical, arranged about an axis 112, and has side ports 104, 106 and 108 extending in different directions therefrom, typically separated by 90 degrees about axis 112. First poll 104 is preferably a male port which preferably meets luer standard ISO 594-1, while second port 106 is configured for incorporating a normally closed swabbable valve which is configured to receive a male luer and third port 108 is preferably a female port, which preferably meets luer standard ISO 594-1. Conventional plugs, nuts and covers may be used in association with polls 104 and 108.

Port 106 of housing element 100 preferably includes a valve employing an elastomeric element 114, held in place by a cap 116, which is welded or otherwise fixed to housing element 100. Elastomeric element 114 and cap 116 are commercially available from Halkey-Roberts Corporation of St. Petersburg. Fla. USA and described in one or more of U.S. Pat. Nos. 6,651,956; 6,089,541 and 6,036,171, the disclosures of which are hereby incorporated by reference. Alternatively, valves and valve elements commercially available from other sources such as Becton-Dickinson, Cardinal, Medegen and Filtertek may be employed.

Ports 104 and 108 are preferably arranged along a mutual longitudinal axis 117 and port 106 is preferably arranged along axis 118, which extends generally perpendicularly to axis 117.

Tubular portion 102 includes a central bore 119 having a slightly conical configuration, which is formed with a circumferential undercut 120. Port 106 defines an interior volume 121, which includes a generally cylindrical bore 122 of a first diameter, adjacent to and extending from central bore 119 and a valve accommodating bore 124 of a second diameter, which is preferably greater than the first diameter, extending generally outwardly of cylindrical bore 122. Cylindrical bore 122 defines a first volume 126 and valve accommodating bore 124 defines a second volume 127. It is noted that elastomeric element 114 is adapted to be fixedly seated between cap 116 and port 106, a portion of the elastomeric element 114 is adapted to be seated within second volume 127 of port 106.

A fluid flow guide 128 preferably bifurcates cylindrical bore 122 of port 106, and extends between the central bore 119 and the elastomeric element 114.

Figure 6A:
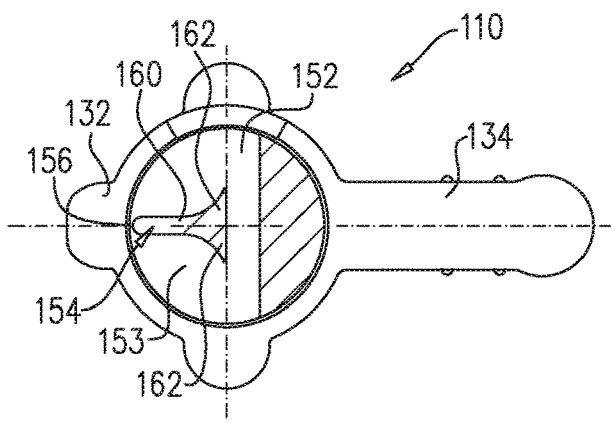
FIGS. 6A, 6B and 6C are sectional illustrations taken along section lines A-A, B-B and C-C in FIG. 4B.
Figure 6B:
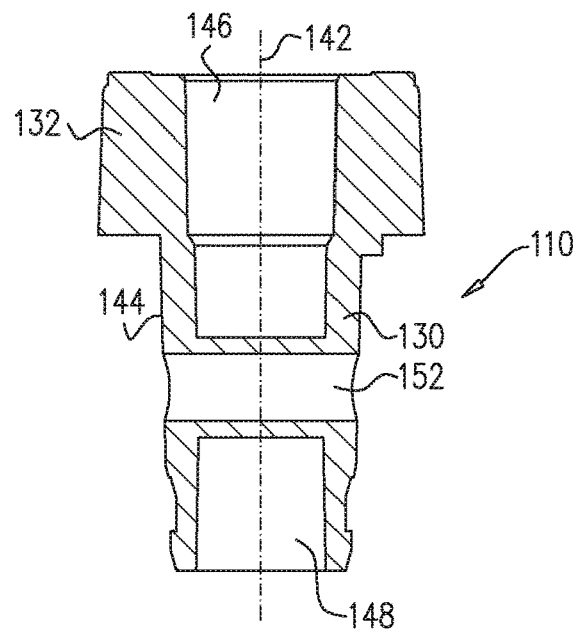
Figure 6C:
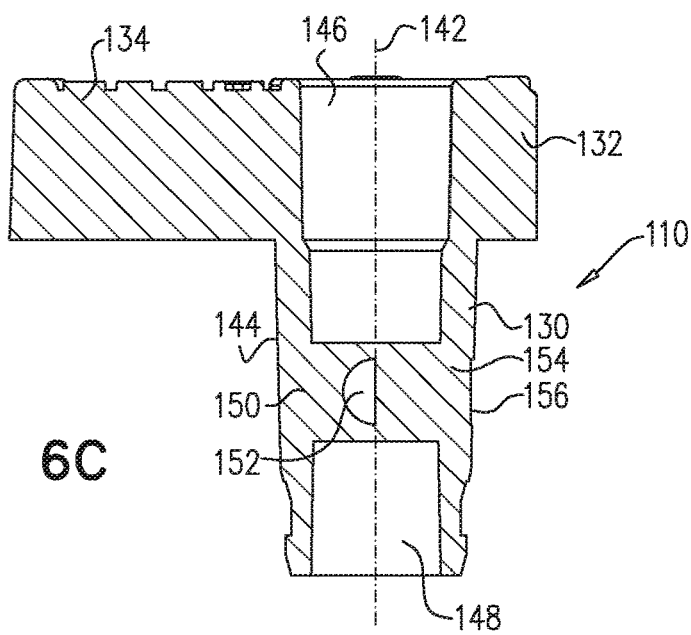

Reference is now made to 4A-5B, which are simplified pictorial illustrations of the handle element 110 forming part of the stopcock of FIG. 1, and to FIGS. 6A-6C, which are sectional illustrations thereof.

As seen in FIGS. 4A-6C, the handle element 110 includes a shaft portion 130, which is integrally formed with a top portion 132 from which extends a finger-engageable protrusion 134. It is appreciated that any other suitable general configuration of the top portion of the handle element may alternatively be employed.

Shaft portion 130 is generally symmetrical about a shaft axis 142 and has a slightly conical outer surface 144, typically having an angle α (as seen particularly in FIG. 5A) of 3-4 degrees, which corresponds to the slightly conical configuration of central bore 119 for rotatable sealing engagement therewith. As seen particularly in FIG. 6C, shaft portion 130 is typically formed with mutually scaled top and bottom cylindrical recesses 146 and 148, which are sealingly separated by a divider 150.

At least one fluid flow passage is provided through handle element 110.

It is a particular feature of an embodiment of the present invention that preferably two fluid flow passages are provided through handle element 110. This enables an increase of a fluid flow rate through the handle element 110. In accordance with an embodiment of the present invention, the fluid flow rate is increased by at least 25%. In accordance with another embodiment of the present invention the fluid flow rate is increased by at least 50%. For example, in a particular embodiment of the present invention the fluid flow rate is increased from 300 ml/min to 600 ml/min.

It is a particular feature of an embodiment of the present invention that the two fluid flow passages are interconnected in some of the mutual relative positions of the handle element 110 and the housing element 100 and that the two fluid flow passages are isolated in other of the mutual relative positions of the handle element 110 and the housing element 100 as described in detail hereinbelow.

Disposed generally between recesses 146 and 148 and sealed therefrom is a side-to-side extending bore 152, selectably defining a first fluid flow passageway between two of the selectable ones of side ports 104, 106 and 108 depending on the rotational orientation of the handle element 110 relative to the housing element 100. It is appreciated that in this particular embodiment, the side-to-side extending bore 152 has a semi-circular cross-section, however it is appreciated that bore 152 can alternatively have any other shape, such as circular, rectangular or other which provides the desired fluid flow rate.

Further disposed generally between recesses 146 and 148 and sealed therefrom is a partially peripherally-extending recess 153, selectably defining a second fluid flow passageway between selectable ones of side ports 104, 106 and 108 depending on the rotational orientation of the handle element 110 relative to the housing element 100. Preferably extending radially and partially bifurcating the recess 153 is a fluid flow guide 154, which is configured for directing the flow of liquid between any of ports 104 and 108 through the second fluid flow passageway defined by recess 153 into the internal volume 121 of port 106 for flushing thereof, when the handle element 110 is suitably positioned. The radially outward facing edge 156 of fluid flow guide 154 is formed with a suitably tapered configuration in order to prevent liquid flow there past when fluid flow guide 154 is not located opposite a port as described in detail hereinbelow. It is noted that the fluid flow guide 154 may alternatively have any other suitable shape, such that the radially outward facing edge 156 thereof can extend towards the inner surface of central bore 119 but slightly spaced therefrom in order to provide minimal fluid flow passage there past when fluid flow guide 154 is not located opposite any of ports 104, 106 and 108.

It is a particular feature of an embodiment of the present invention that fluid communication between opposite ends of bore 152 occurs in parallel to fluid communication along recess 153 at least in some of the mutual relative positions of the handle element 110 and the housing element 100.

Fluid flow guide 154 directs the flow of liquid between ports 104 and 108 through recess 153 and into the internal volume 121 of port 106 for flushing thereof, when the handle element 110 is suitably positioned. Simultaneously, fluid flow is directed between ports 104 and 108 through bore 152, thereby increasing the fluid flow rate through the stopcock of FIG. 1.

It is specifically seen in FIG. 6A that in accordance with an embodiment of the present invention, the fluid flow guide 154 is formed as a generally flat wall 160, which is adapted to extend up to the inner surface of the inner bore 119 of housing element 100 and a generally wider arcuate concave portion 162 formed on each side of the flat wall 160 and extending slightly outwardly therefrom. In this particular embodiment, the concave portion 162 of fluid flow guide 154 is located adjacent bore 152 and typically extends along a relatively minor longitudinal extent of bore 152.

Figure 7:
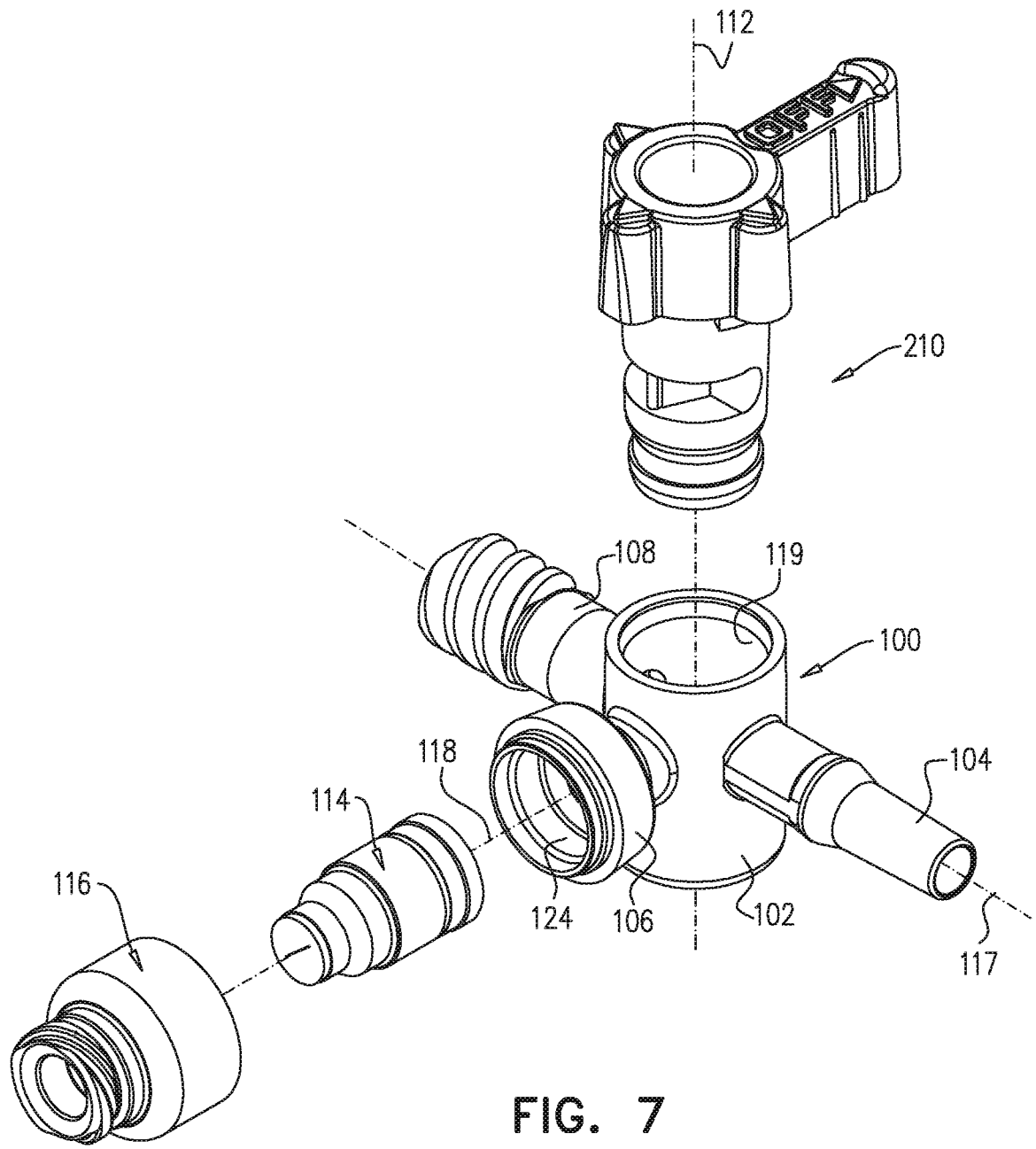
FIG. 7 is a simplified exploded view illustration of a stopcock constructed and operative in accordance with another embodiment of the present invention.
Figure 8A:
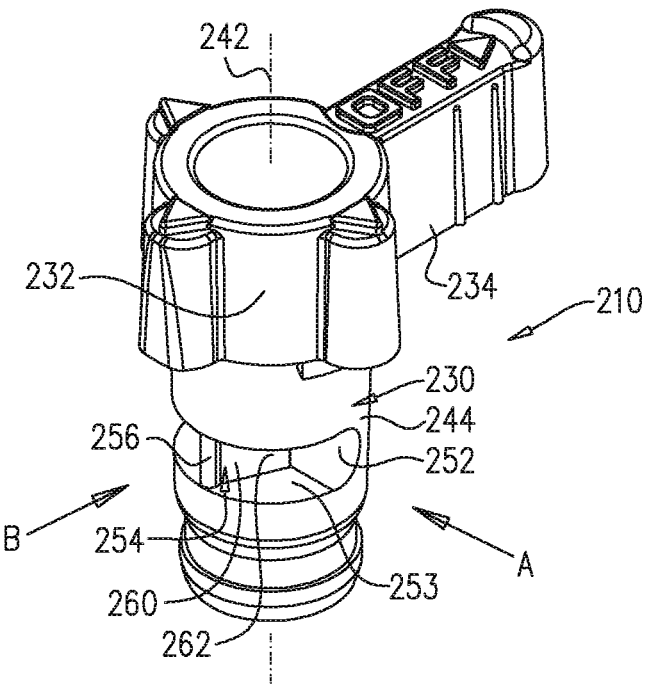
FIGS. 8A & 8B are simplified pictorial illustrations of a handle element, which forms part of the stopcock of FIG. 7 taken in two orientations.
Figure 8B:
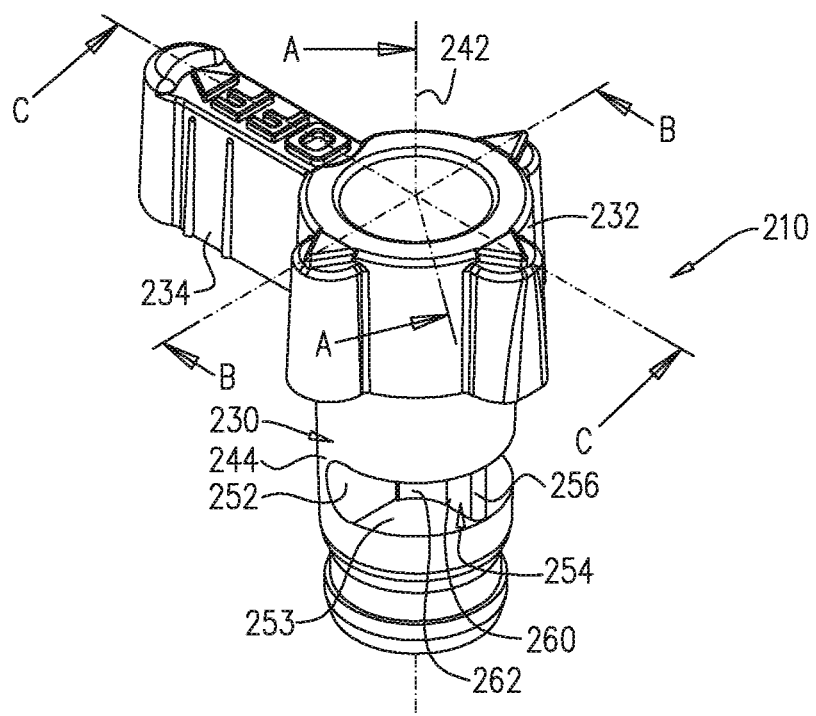
Figure 9A:
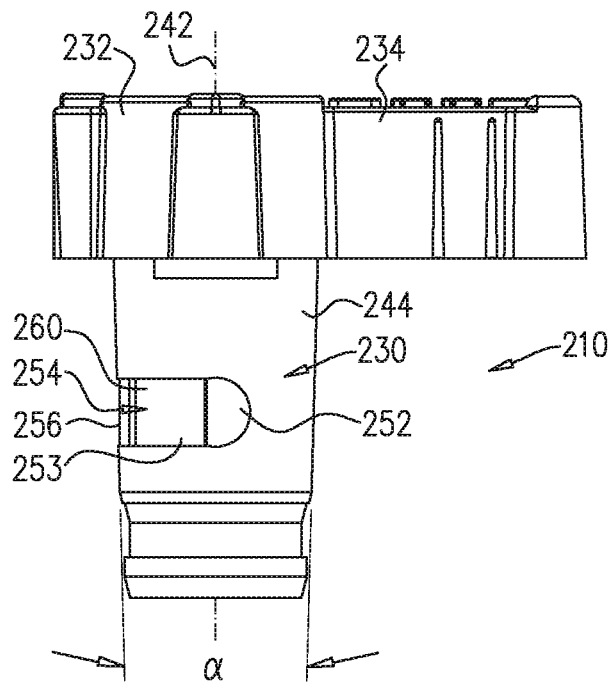
FIGS. 9A & 9B are simplified plan view illustrations of the handle element of FIGS. 8A & 8B taken along respective directions A and B in FIG. 8A.
Figure 9B:
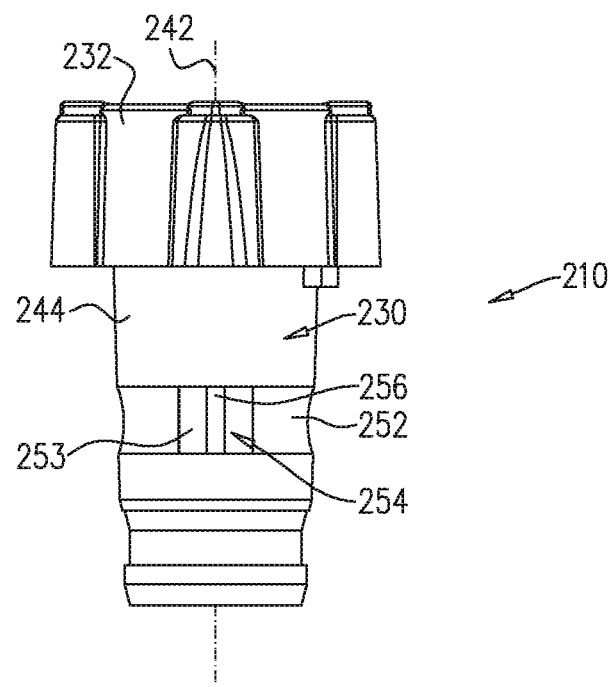

Reference is now made to FIG. 7, which is a simplified exploded view illustration of a stopcock constructed and operative in accordance with another embodiment of the present invention.

As seen in FIG. 7, the stopcock comprises a housing element 100, which is preferably identical in all respects to housing element 100 which is illustrated and described with respect to FIGS. 2A-3B. The housing element 100 includes a main tubular portion 102 and three side ports, designated by reference numerals 104, 106 and 108 respectively. A handle element 210 in accordance with another embodiment of the present invention is arranged to be seated within main tubular portion 102 of housing element 100. It is also noted that a similar elastomeric element 114 and cap 116 are adapted to be seated within port 106 of the housing element 100, in a similar manner as described with respect to FIGS. 1-3B.

Figure 10A:
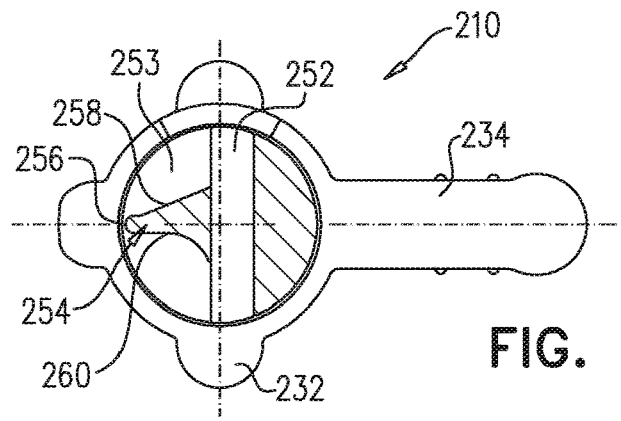
FIGS. 10A, 10B and 10C are sectional illustrations taken along section lines A-A, B-B and C-C in FIG. 8B.
Figure 10B:
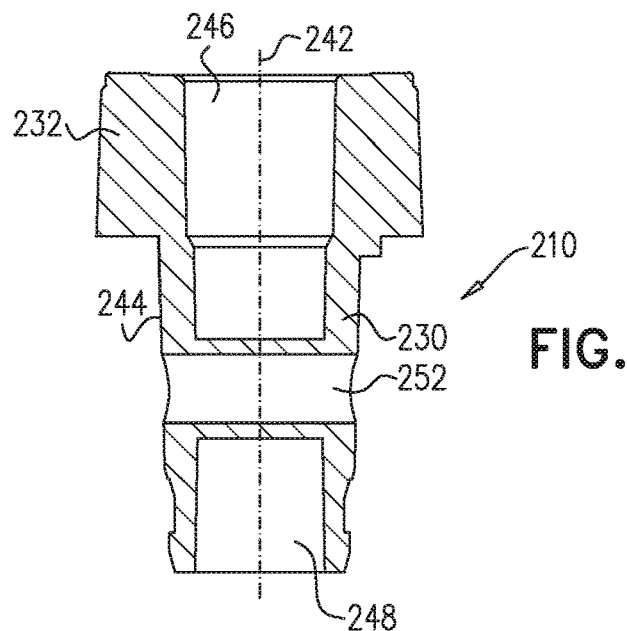
Figure 10C:
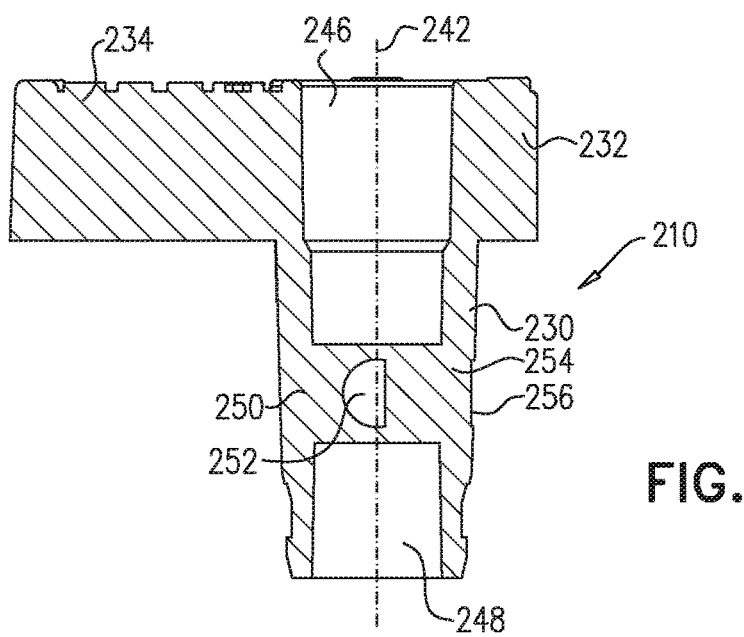

Reference is now made to FIGS. 8A-9B, which are simplified pictorial illustrations of the handle element 210 forming part of the stopcock of FIG. 7 and to FIGS. 10A-10C, which are sectional illustrations thereof.

Shaft portion 230 is generally symmetrical about a shaft axis 242 and has a slightly conical outer surface 244, typically having an angle α (as seen particularly in FIG. 9A) of 3-4 degrees, which corresponds to the slightly conical configuration of central bore 119 for rotatable sealing engagement therewith. As seen particularly in FIG. 10C, shaft portion 230 is typically formed with mutually sealed top and bottom cylindrical recesses 246 and 248, which are sealingly separated by a divider 250.

At least one fluid flow passage is provided through handle element 210.

It is a particular feature of an embodiment of the present invention that preferably two fluid flow passages are provided through handle element 210. This enables an increase of a fluid flow rate through the handle element 210. In accordance with an embodiment of the present invention, the fluid flow rate is increased by at least 25%. In accordance with another embodiment of the present invention the fluid flow rate is increased by at least 50%. For example, in a particular embodiment of the present invention the fluid flow rate is increased from 300 ml/min to 600 ml/min.

It is a particular feature of an embodiment of the present invention that the two fluid flow passages are interconnected in some of the mutual relative positions of the handle element 210 and the housing element 100 and that the two fluid flow passages are isolated in other of the mutual relative positions of the handle element 210 and the housing element 100 as described in detail hereinbelow.

Disposed generally between recesses 246 and 248 and sealed therefrom is a side-to-side extending bore 252, selectably defining a first fluid flow passageway between two of the selectable ones of side ports 104, 106 and 108 depending on the rotational orientation of the handle element 210 relative to the housing element 100. It is appreciated that in this particular embodiment, the side-to-side extending bore 252 has a semi-circular cross-section, however it is appreciated that bore 252 can alternatively have any other shape, such as circular, rectangular or other which provides the desired fluid flow rate.

Further disposed generally between recesses 246 and 248 and sealed therefrom is a partially peripherally-extending recess 253, selectably defining a second fluid flow passageway between selectable ones of side ports 104, 106 and 108 depending on the rotational orientation of the handle element 210 relative to the housing element 100. Preferably extending radially and partially bifurcating the recess 253 is a fluid flow guide 254, which is configured for directing the flow of liquid between any of ports 104 and 108 through the second fluid flow passageway defined by recess 253 into the internal volume 121 of port 106 for flushing thereof, when the handle element 210 is suitably positioned.

The radially outward facing edge 256 of fluid flow guide 254 extends preferably towards the inner surface of central bore 119 but is slightly spaced therefrom in order to provide minimal fluid flow passage there past when fluid flow guide 254 is not located opposite a port as shown and described in detail hereinbelow. The fluid flow guide 254 may alternatively have many other shapes such that the radially outward facing edge 256 of fluid flow guide 254 is formed with a suitably tapered configuration in order to prevent liquid flow there past when fluid flow guide 254 is not located opposite any of ports 104, 106 and 108.

It is a particular feature of an embodiment of the present invention that fluid communication between opposite ends of bore 252 occurs in parallel to fluid communication along recess 253 at least in some of the mutual relative positions of the handle element 210 and housing element 100.

Fluid flow guide 254 directs the flow of liquid between ports 104 and 108 through recess 253 and into the internal volume 121 of port 106 for flushing thereof, when the handle element 210 is suitably positioned. Simultaneously, fluid flow is directed between ports 104 and 108 through bore 252, thereby increasing the fluid flow rate through the stopcock of FIG. 7.

It is specifically seen in FIG. 10A that in accordance with an embodiment of the present invention, the fluid flow guide 254 in accordance with an embodiment of the present invention is formed as a fin having one generally straight inclined wall surface 258 and another generally concave wall surface 260, as specifically seen in FIG. 10A, both walls 258 and 260 are joined at the radially outward facing edge 256, which is adapted to extend to the vicinity of the inner surface of inner bore 119 of housing element 100. Both the inclined wall surface 258 and the concave wall surface 260 extend from the radially outward facing edge 256 to the vicinity of bore 252 and typically extend along a relatively minor longitudinal extent of bore 252.

Figure 11:
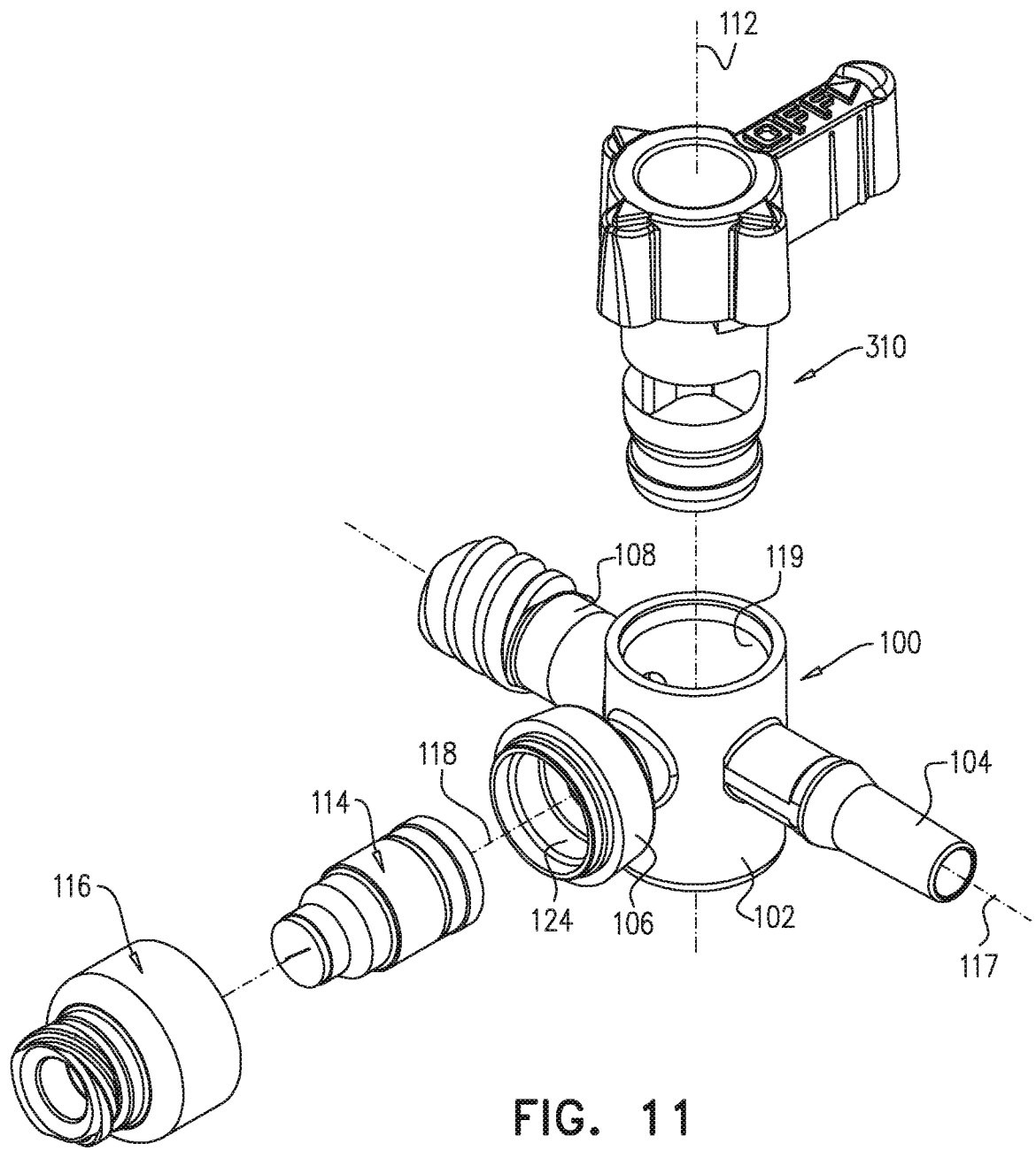
FIG. 11 is a simplified exploded view illustration of a stopcock constructed and operative in accordance with still another embodiment of the present invention.
Figure 12A:
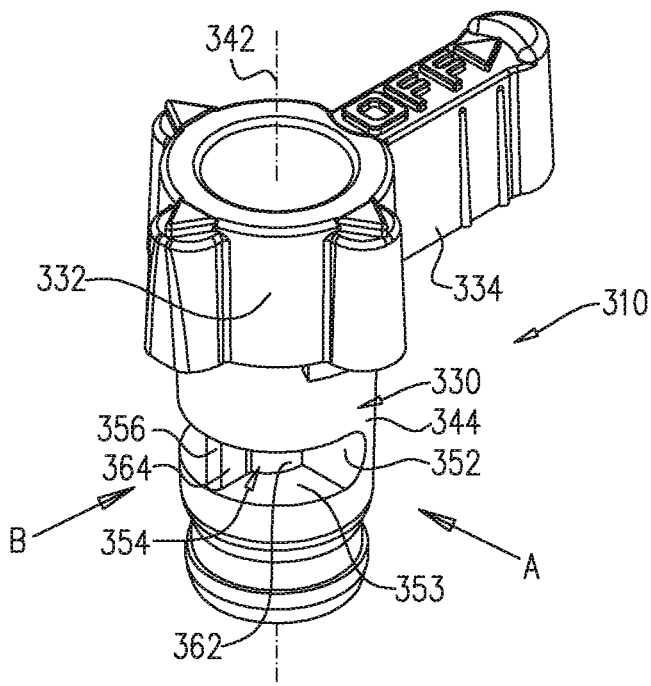
FIGS. 12A & 12B are simplified pictorial illustrations of a handle element, which forms part of the stopcock of FIG. 11 taken in two orientations.
Figure 12B:
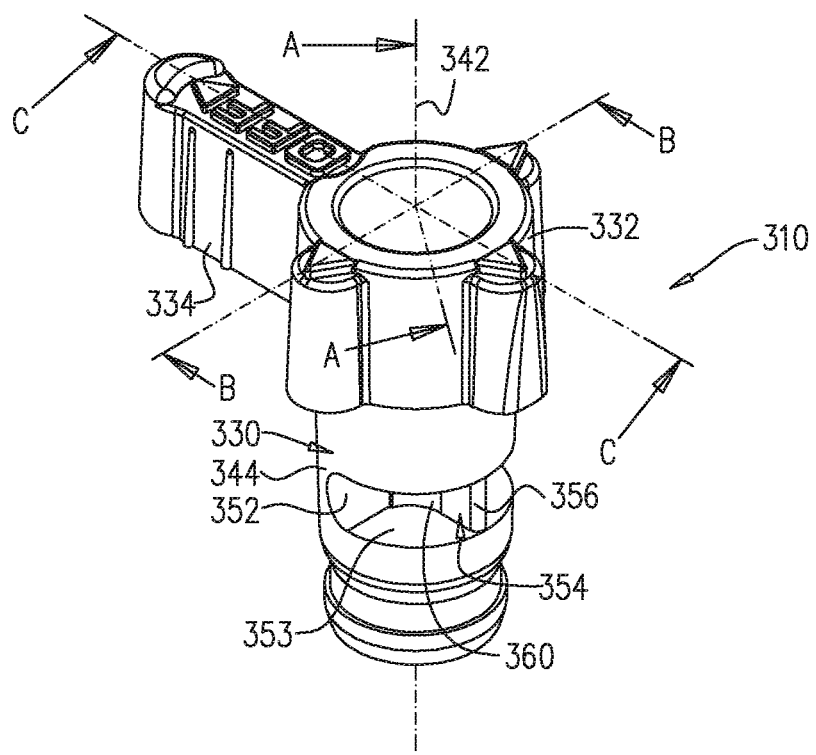
Figure 13A:
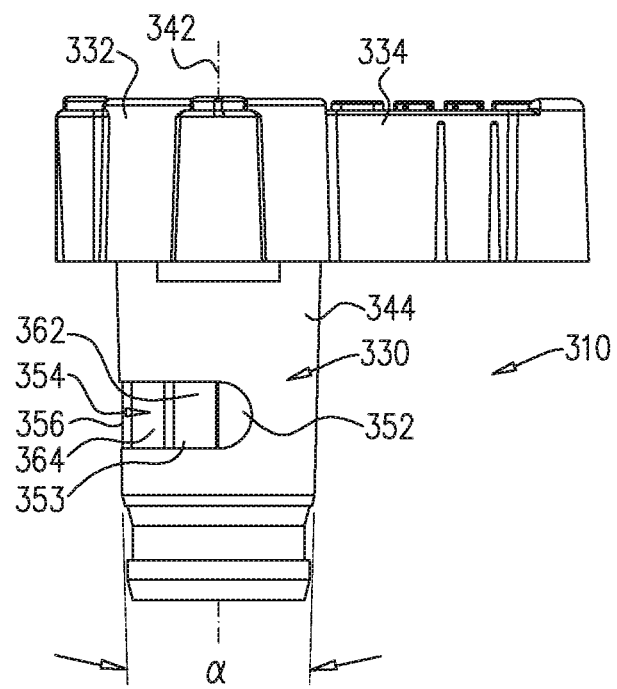
FIGS. 13A & 13B are simplified plan view illustrations of the handle element of FIGS. 12A & 12B taken along respective directions A and B in FIG. 12A.
Figure 13B:
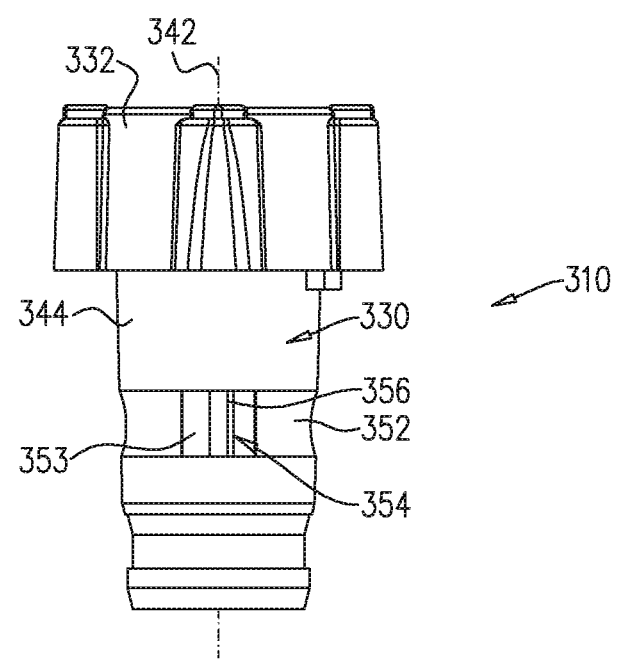

Reference is now made to FIG. 11, which is a simplified exploded view illustration of a stopcock constructed and operative in accordance with still another embodiment of the present invention.

As seen in FIG. 11, the stopcock comprises a housing element 100, which is preferably identical in all respects to housing element 100 which is illustrated and described with respect to FIGS. 2A-3B. The housing element 100 includes a main tubular portion 102 and three side ports, designated by reference numerals 104, 106 and 108 respectively. A handle element 310 in accordance with still another embodiment of the present invention is arranged to be seated within main tubular portion 102 of housing element 100. It is also noted that a similar elastomeric element 114 and cap 116 are adapted to be seated within port 106 of the housing element 100, in a similar manner as described with respect to FIGS. 1-3B.

Figure 14A:
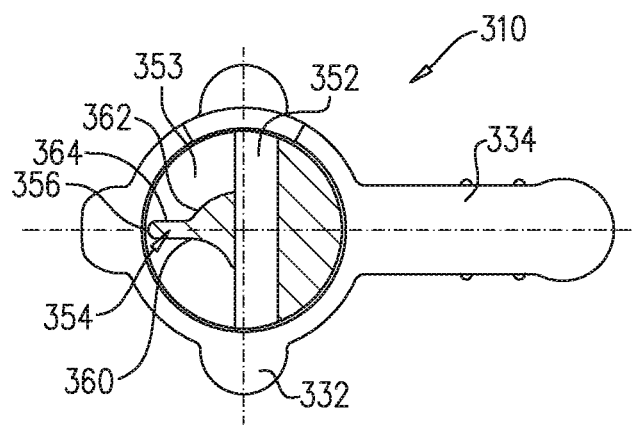
FIGS. 14A, 14B and 14C are sectional illustrations taken along section lines A-A, B-B and C-C in FIG. 12B.
Figure 14B:
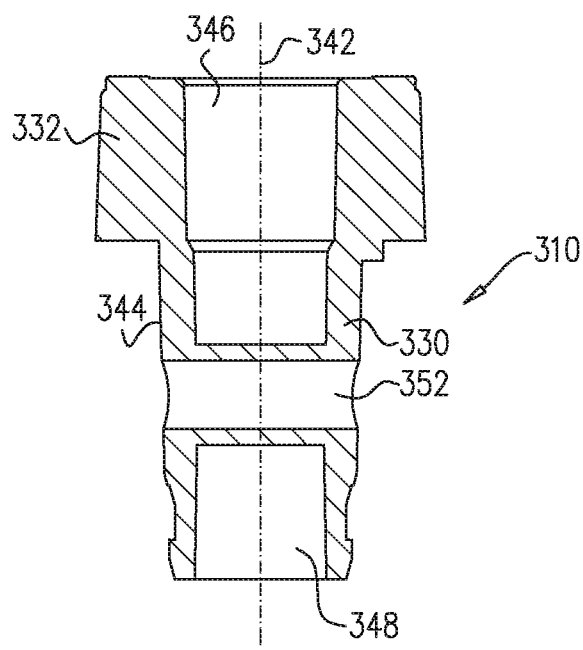
Figure 14C:
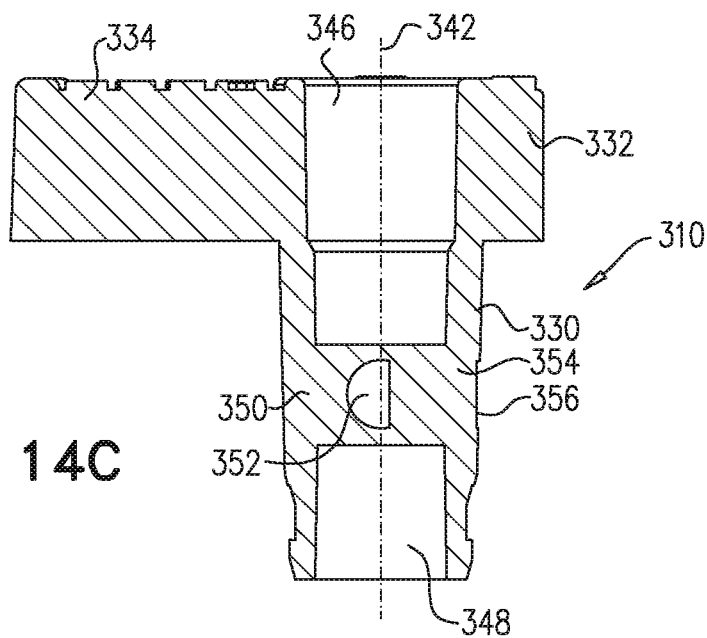

Reference is now made to FIGS. 12A-13B, which are simplified pictorial illustrations of the handle element 310 forming part of the stopcock of FIG. 11 and to FIGS. 14A-14C, which are sectional illustrations thereof.

Shaft portion 330 is generally symmetrical about a shaft axis 342 and has a slightly conical outer surface 344, typically having an angle α (as seen particularly in FIG. 13A) of 3-4 degrees, which corresponds to the slightly conical configuration of central bore 119 for rotatable sealing engagement therewith. As seen particularly in FIG. 14C, shaft portion 330 is typically formed with mutually sealed top and bottom cylindrical recesses 346 and 348, which are sealingly separated by a divider 350.

At least one fluid flow passage is provided through handle element 310.

It is a particular feature of an embodiment of the present invention that preferably two fluid flow passages are provided through handle element 310. This enables an increase of a fluid flow rate through the handle element 310. In accordance with an embodiment of the present invention, the fluid flow rate is increased by at least 25%. In accordance with another embodiment of the present invention the fluid flow rate is increased by at least 50%. For example, in a particular embodiment of the present invention the fluid flow rate is increased from 300 ml/min to 600 ml/min.

It is a particular feature of an embodiment of the present invention that the two fluid flow passages are interconnected in some of the mutual relative positions of the handle element 310 and the housing element 100 and that the two fluid flow passages are isolated in other of the mutual relative positions of the handle element 310 and the housing element 100 as described in detail hereinbelow.

Disposed generally between recesses 346 and 348 and sealed therefrom is a side-to-side extending bore 352, selectably defining a first fluid flow passageway between two of the selectable ones of side ports 104, 106 and 108 depending on the rotational orientation of the handle element 310 relative to the housing element 100. It is appreciated that in this particular embodiment, the side-to-side extending bore 352 has a semi-circular cross-section, however it is appreciated that bore 352 can alternatively have any other shape, such as circular, rectangular or other which provides the desired fluid flow rate.

Further disposed generally between recesses 346 and 348 and sealed therefrom is a partially peripherally-extending recess 353, selectably defining a second fluid flow passageway between selectable ones of side ports 104, 106 and 108 depending on the rotational orientation of the handle element 310 relative to the housing element 100. Preferably extending radially and partially bifurcating the recess 353 is a fluid flow guide 354, which is configured for directing the flow of liquid between any of ports 104 and 108 through the second fluid flow passageway defined by recess 353 into the internal volume 121 of port 106 for flushing thereof, when the handle element 310 is suitably positioned.

The radially outward facing edge 356 of fluid flow guide 354 extends preferably towards the inner surface of central bore 119 but is slightly spaced therefrom in order to provide minimal fluid flow passage there past when fluid flow guide 354 is not located opposite a port as shown and described in detail hereinbelow. The fluid flow guide 354 may alternatively have many other shapes such that the radially outward facing edge 356 of fluid flow guide 354 is formed with a suitably tapered configuration in order to prevent liquid flow there past when fluid flow guide 354 is not located opposite any of ports 104, 106 and 108.

It is a particular feature of an embodiment of the present invention that fluid communication between opposite ends of bore 352 occurs in parallel to fluid communication along recess 353 at least in part of the mutual relative positions of the handle element 310 and housing element 100.

Fluid flow guide 354 directs the flow of liquid between ports 104 and 108 through recess 353 and into the internal volume 121 of port 106 for flushing thereof, when the handle element 310 is suitably positioned. Simultaneously, fluid flow is directed between ports 104 and 108 through bore 352, thereby increasing the fluid flow rate through the stopcock of FIG. 11.

It is specifically seen in FIG. 14A that in accordance with an embodiment of the present invention, the fluid flow guide 354 in accordance with an embodiment of the present invention is formed as a fin having one generally concave wall surface 360 and another generally convex wall surface 362 connected with a generally straight wall surface 364. The straight wall surface 364 and the concave wall surface 360 are joined at the radially outward facing edge 356, which is adapted to extend to the vicinity of the inner surface of inner bore 119 of housing element 100. Both the convex wall surface 362 and the concave wall surface 360 extend from the radially outward facing edge 356 to the vicinity of bore 352 and typically extend along a relatively minor longitudinal extent of bore 352.

Figure 15:
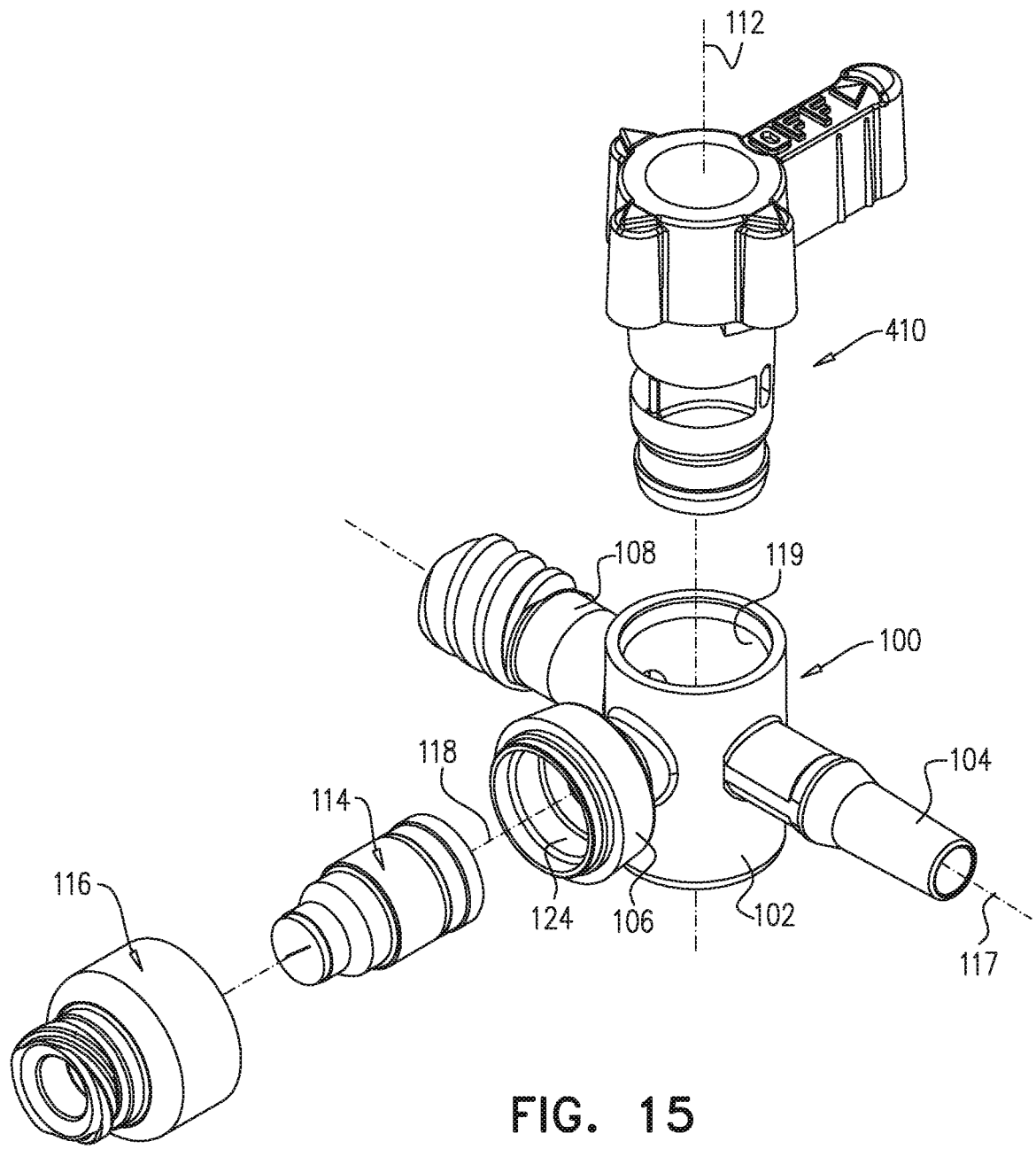
FIG. 15 is a simplified exploded view illustration of a stopcock constructed and operative in accordance with yet another embodiment of the present invention.
Figure 16A:
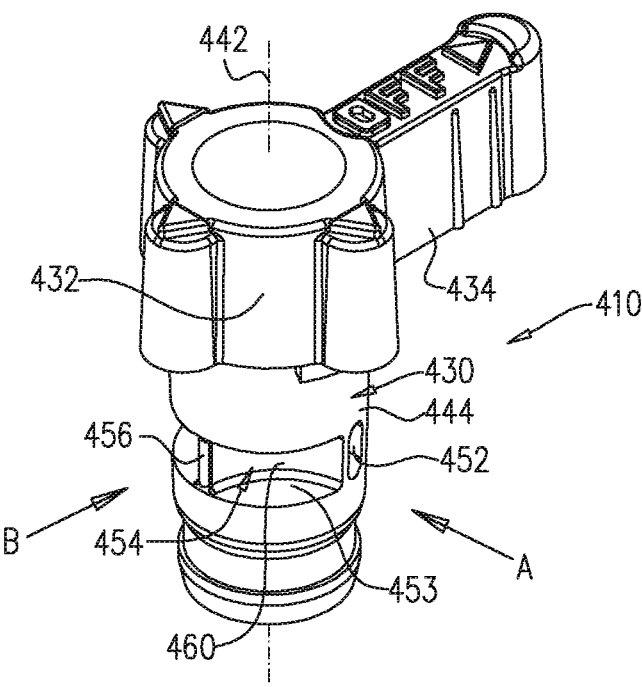
FIGS. 16A & 16B are simplified pictorial illustrations of a handle element, which forms part of the stopcock of FIG. 15 taken in two orientations.
Figure 16B:
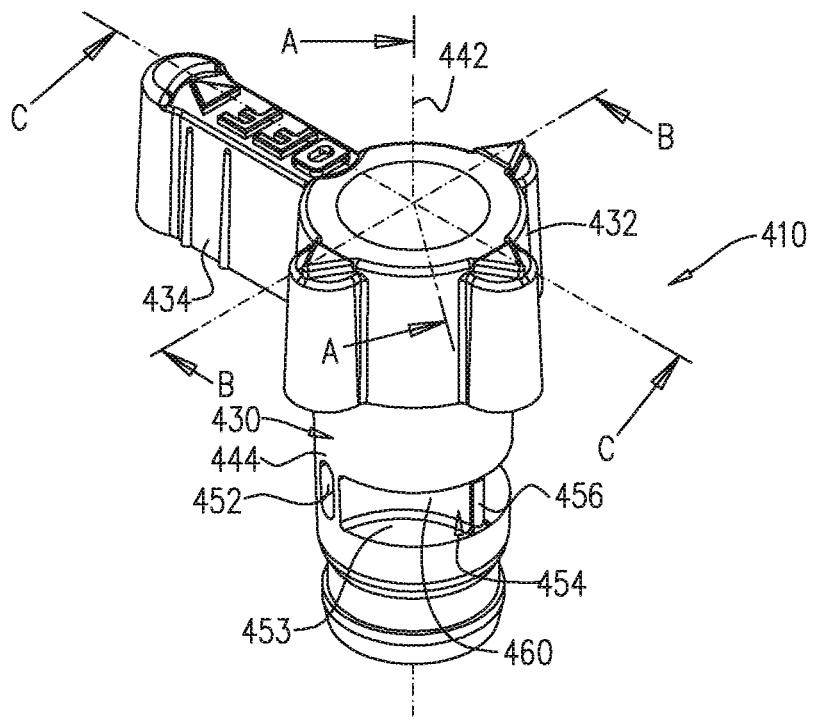
Figure 17A:
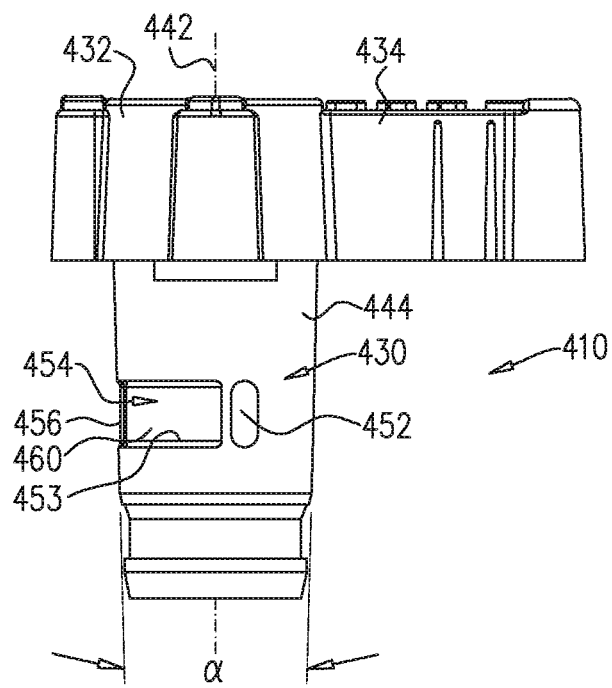
FIGS. 17A & 17B are simplified plan view illustrations of the handle element of FIGS. 16A & 16B taken along respective directions A and B in FIG. 16A.
Figure 17B:
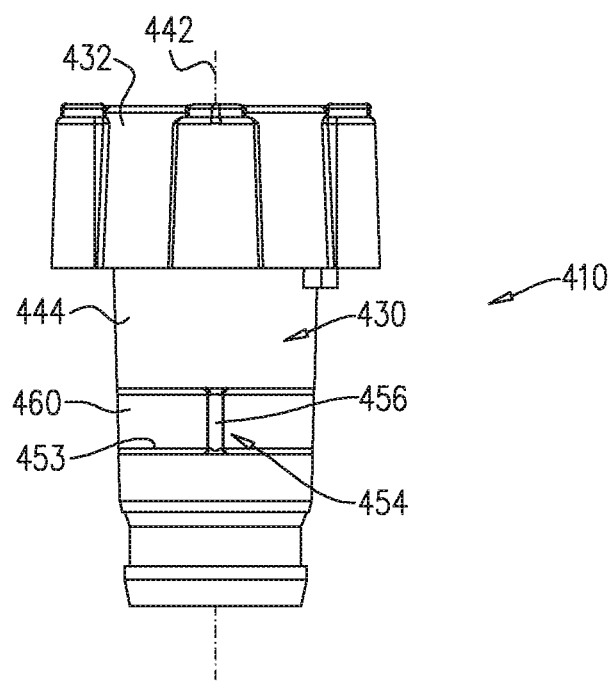

Reference is now made to FIG. 15, which is a simplified exploded view illustration of a stopcock constructed and operative in accordance with yet another embodiment of the present invention.

As seen in FIG. 15, the stopcock comprises a housing element 100, which is preferably identical in all respects to housing element 100 which is illustrated and described with respect to FIGS. 2A-3B. The housing element 100 includes a main tubular portion 102 and three side ports, designated by reference numerals 104, 106 and 108 respectively. A handle element 410 in accordance with still another embodiment of the present invention is arranged to be seated within main tubular portion 102 of housing element 100. It is also noted that a similar elastomeric element 114 and cap 116 are adapted to be seated within port 106 of the housing element 100, in a similar manner as described with respect to FIGS. 1-3B.

Figure 18A:
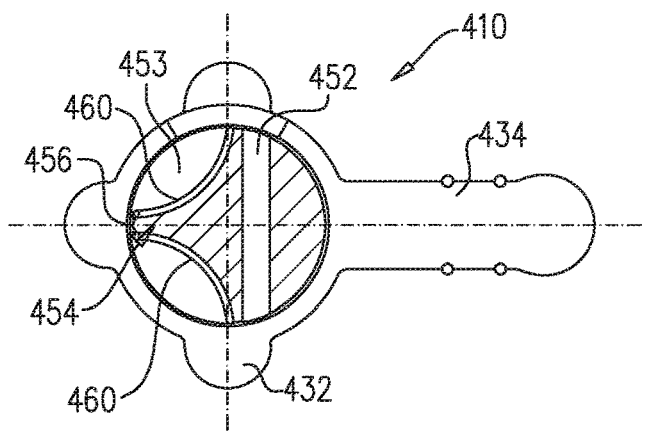
FIGS. 18A, 18B and 18C are sectional illustrations taken along section lines A-A, B-B and C-C in FIG. 16B.
Figure 18B:
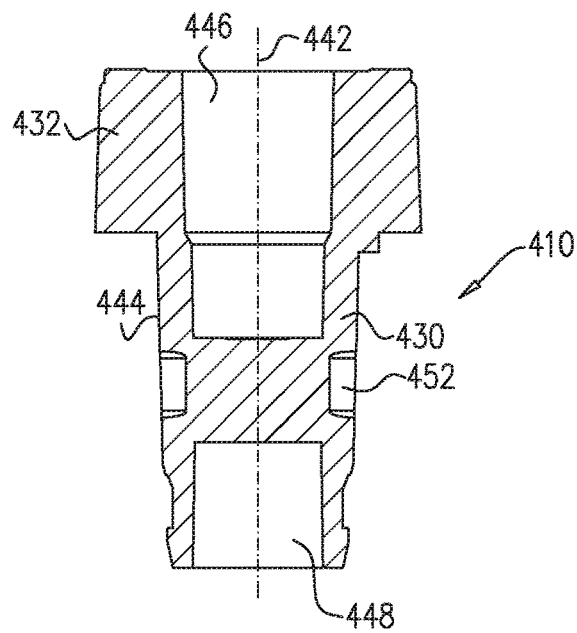
Figure 18C:
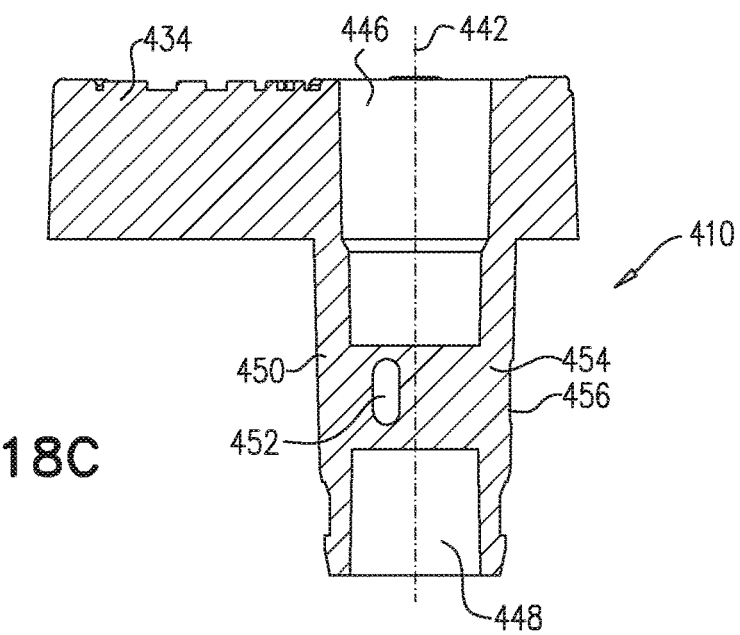

Reference is now made to FIGS. 16A-17B, which are simplified pictorial illustrations of the handle element 410 forming part of the stopcock of FIG. 15 and to FIGS. 18A-18C, which are sectional illustrations thereof.

Shaft portion 430 is generally symmetrical about a shaft axis 442 and has a slightly conical outer surface 444, typically having an angle α (as seen particularly in FIG. 17A) of 3-4 degrees, which corresponds to the slightly conical configuration of central bore 119 for rotatable sealing engagement therewith. As seen particularly in FIG. 18C, shaft portion 430 is typically formed with mutually sealed top and bottom cylindrical recesses 446 and 448, which are sealingly separated by a divider 450.

At least one fluid flow passage is provided through handle element 410.

It is a particular feature of an embodiment of the present invention that preferably two fluid flow passages are provided through handle element 410. This enables an increase of a fluid flow rate through the handle element 410. In accordance with an embodiment of the present invention, the fluid flow rate is increased by at least 25%. In accordance with another embodiment of the present invention the fluid flow rate is increased by at least 50%. For example, in a particular embodiment of the present invention the fluid flow rate is increased from 300 ml/min to 600 ml/min.

It is a particular feature of an embodiment of the present invention that the two fluid flow passages are interconnected in some of the mutual relative positions of the handle element 410 and the housing element 100 and that the two fluid flow passages are isolated in other of the mutual relative positions of the handle element 410 and the housing element 100 as described in detail hereinbelow.

Disposed generally between recesses 446 and 448 and sealed therefrom is a side-to-side extending bore 452, selectably defining a first fluid flow passageway between two of the selectable ones of side ports 104, 106 and 108 depending on the rotational orientation of the handle element 410 relative to the housing element 100. It is appreciated that in this particular embodiment, the side-to-side extending bore 452 has an obround cross-section, however it is appreciated that bore 452 can alternatively have any other shape, such as circular, rectangular or other which provides the desired fluid flow rate.

Further disposed generally between recesses 446 and 448 and sealed therefrom is a partially peripherally-extending recess 453, selectably defining a second fluid flow passageway between selectable ones of side ports 104, 106 and 108 depending on the rotational orientation of the handle element 410 relative to the housing element 100. Preferably extending radially and partially bifurcating the recess 453 is a fluid flow guide 454, which is configured for directing the flow of liquid between any of ports 104 and 108 through the second fluid flow passageway defined by recess 453 into the internal volume 121 of poll 106 for flushing thereof, when the handle element 410 is suitably positioned.

The radially outward facing edge 456 of fluid flow guide 454 extends preferably towards the inner surface of central bore 119 but is slightly spaced therefrom in order to provide minimal fluid flow passage there past when fluid flow guide 454 is not located opposite a port as shown and described in detail hereinbelow. The fluid flow guide 454 may alternatively have many other shapes such that the radially outward facing edge 456 of fluid flow guide 454 is formed with a suitably tapered configuration in order to prevent liquid flow there past when fluid flow guide 454 is not located opposite any of ports 104, 106 and 108.

It is a particular feature of an embodiment of the present invention that fluid communication between opposite ends of bore 452 occurs in parallel to fluid communication along recess 453, at least in some operating positions of the stopcock of FIG. 15 at least in some of the mutual relative positions of the handle element 410 and housing element 100.

Fluid flow guide 454 directs the flow of liquid between ports 104 and 108 through recess 453 and into the internal volume 121 of port 106 for flushing thereof, when the handle element 410 is suitably positioned. Simultaneously, fluid flow is directed between ports 104 and 108 through bore 452, thereby increasing the fluid flow rate through the stopcock of FIG. 15.

It is specifically seen in FIG. 18A that in accordance with an embodiment of the present invention, the fluid flow guide 454 in accordance with an embodiment of the present invention is formed as a wedge having two symmetric generally concave wall surfaces 460. The concave wall surfaces 460 are joined at the radially outward facing edge 456, which is adapted to extend to the vicinity of the inner surface of inner bore 119 of housing element 100. The concave wall surfaces 460 extend from the radially outward facing edge 456 to the vicinity of bore 452 and typically extend along a relatively major longitudinal extent of bore 452, preferably along the entire longitudinal extent of bore 452.

It is noted that the concave wall surfaces 460 extend from the outward facing edge 456 towards the inner surface of the central bore 119 of main tubular portion 102 of the housing element 100, as seen and described in more detail hereinbelow.

It is a particular feature of an embodiment of the present invention bore 452 is generally spaced from recess 453 by fluid flow guide 454, therefore the first fluid flow passage is generally isolated from the second fluid flow passage at least in some of the mutual relative positions of the handle element 410 and housing element 100.

References is now made to FIGS. 19A, 19B, 19C and 19D, which are simplified assembled pictorial illustrations of the stopcock of FIG. 1 in four operative orientations and to FIGS. 20A, 208, 20C and 20D, which are sectional illustrations of the stopcock having the handle shown in FIGS. 4A-6C, taken along section lines A-A, B-B, C-C and D-D in FIGS. 19A, 19B, 19C and 19D respectively.

It is noted that port 104 is preferably connected to a patient, port 108 is preferably connected through an IV set to an infusion bag and port 106 is preferably adapted for insertion of a medical instrument, such as a syringe thereinto.

Figure 19A:
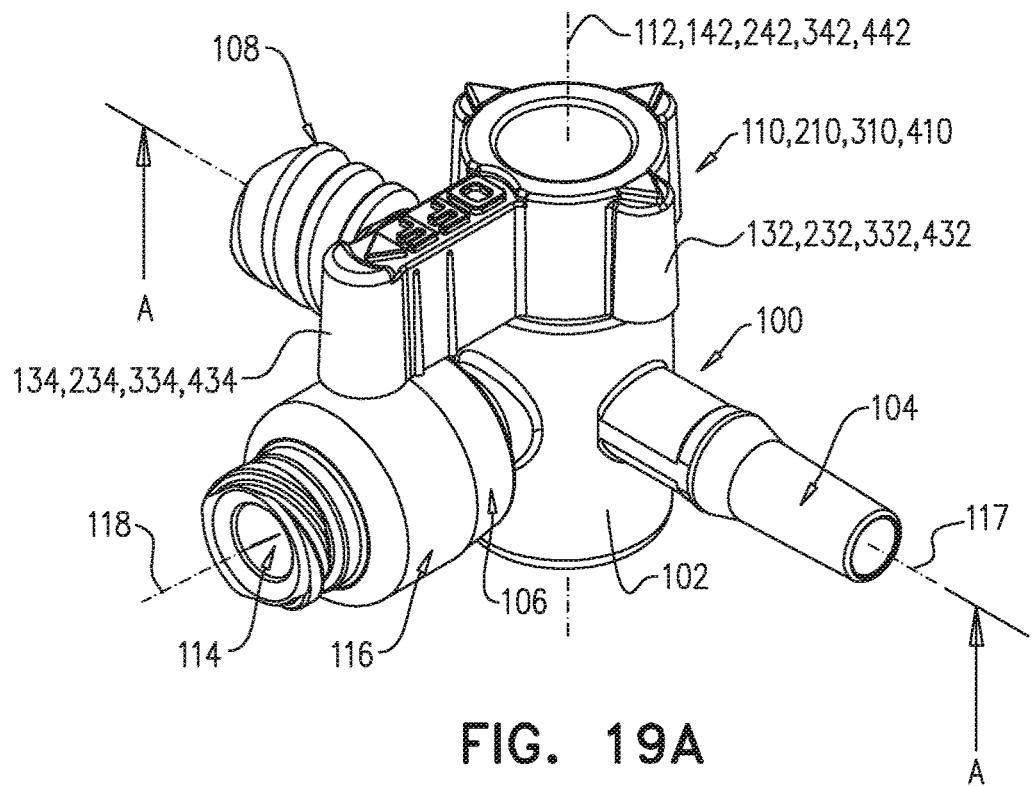
FIGS. 19A, 19B, 19C and 19D are simplified assembled pictorial illustrations of the stopcock of FIG. 1 in four operative orientations.
Figure 20A:
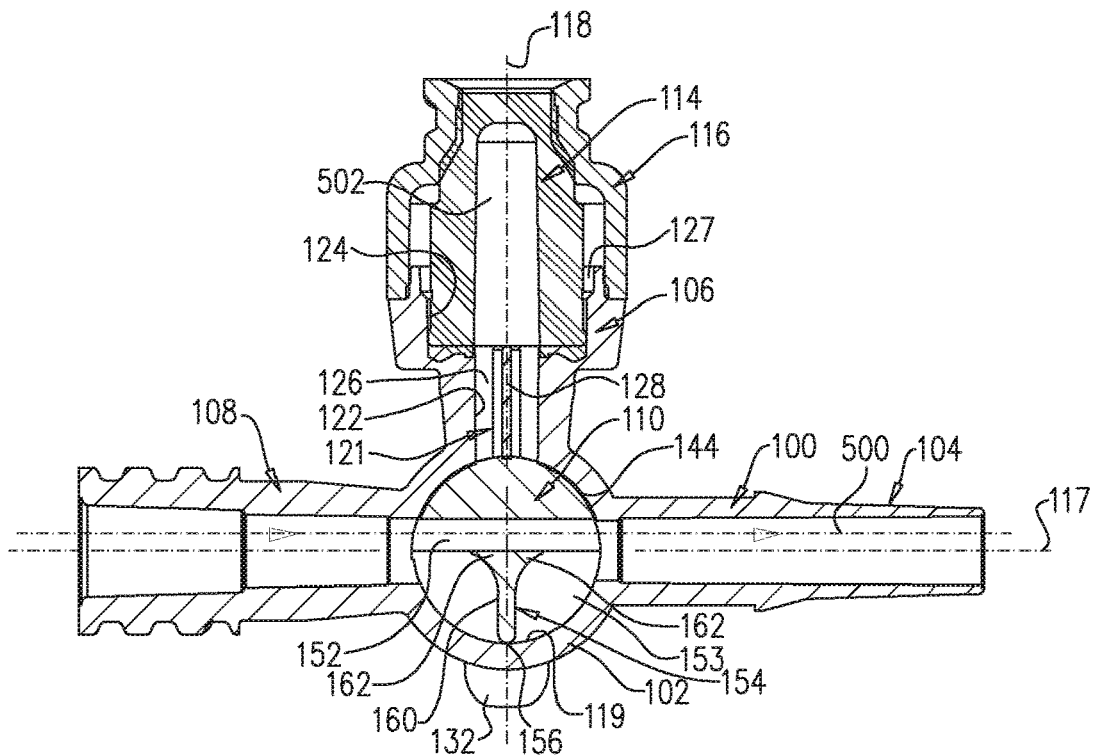
FIGS. 20A, 20B, 20C and 20D are sectional illustrations of a stopcock having the handle shown in FIGS. 4A-6C, taken along section lines A-A, B-B, C-C and D-D in FIGS. 19A, 19B, 19C and 19D respectively.

FIGS. 19A and 20A illustrate a first operating position of the stopcock of FIG. 1, which is typically employed for blood pressure monitoring by means of a pressure transducer, where there should be no contact of fluid with the elastomeric element 114. In this first operating position, the handle element 110 is rotatably disposed within the main tubular portion 102 of the housing element 100, such that finger engageable protrusion 134 is aligned with port 106 of the housing element 100 and extends along an axis, which is parallel to axis 118.

As seen in FIG. 20A, there is a fluid communication between ports 104 and 108 through first fluid flow passage defined by side-to-side extending bore 152, as indicated by an arrow 500. Liquid communication from port 108 to port 104 through second fluid flow passage, defined by recess 153, past fluid flow guide 154 is prevented, because it is blocked by fluid flow guide 154, whose edge 156 sealingly engages an inner facing wall of central bore 119 of housing element 100. This orientation may be utilized to provide fluid flow between ports 104 and 108 only.

It is appreciated that first fluid flow passage allows liquid communication between port 104 and 108 and liquid communication along the second fluid flow passage, particularly along recess 153, in this orientation is preferably blocked.

Alternatively, in accordance with another embodiment of the present invention, the fluid flow guide 154 can extend toward the inner facing wall of central bore 119 of housing element 100, whereas the edge 156 is slightly spaced therefrom in order to allow minimal fluid flow passage through the second fluid flow passage, along recess 153 and around fluid flow guide 154.

It is noted that liquid communication between port 104 and 108 through side-to-side bore 152 is sufficient for the purpose of pressure monitoring, while avoiding dampening of the signal, which could have occurred if the fluid would come in contact with elastomeric element 114.

Figure 19B:
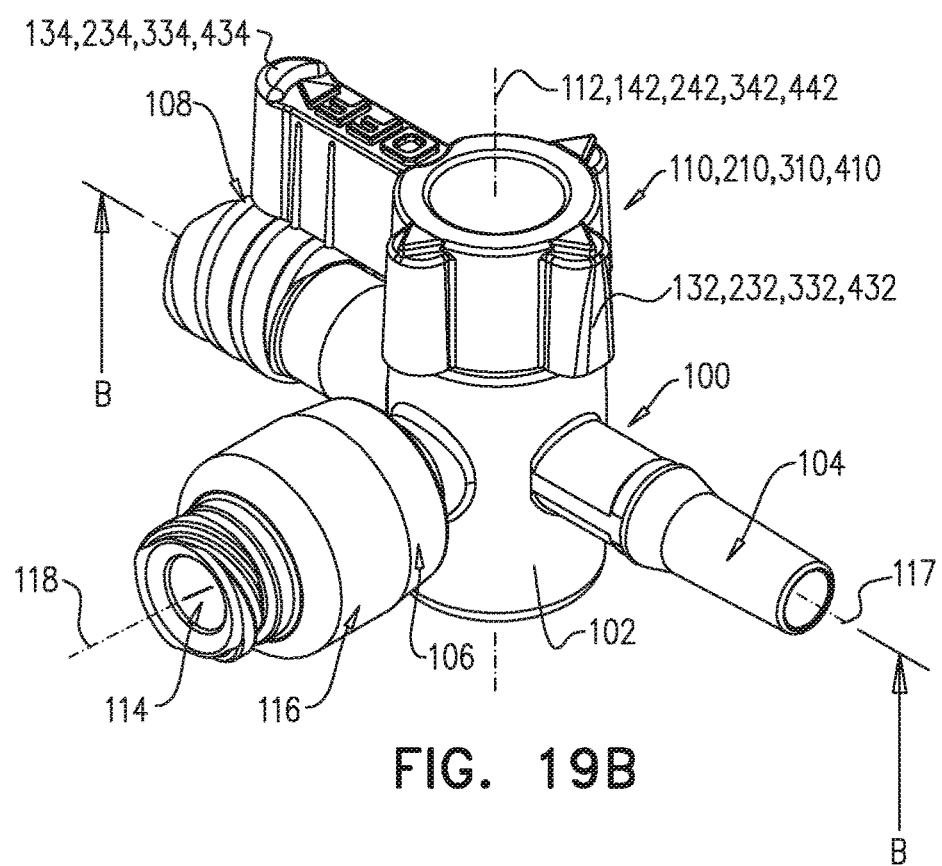
Figure 20B:
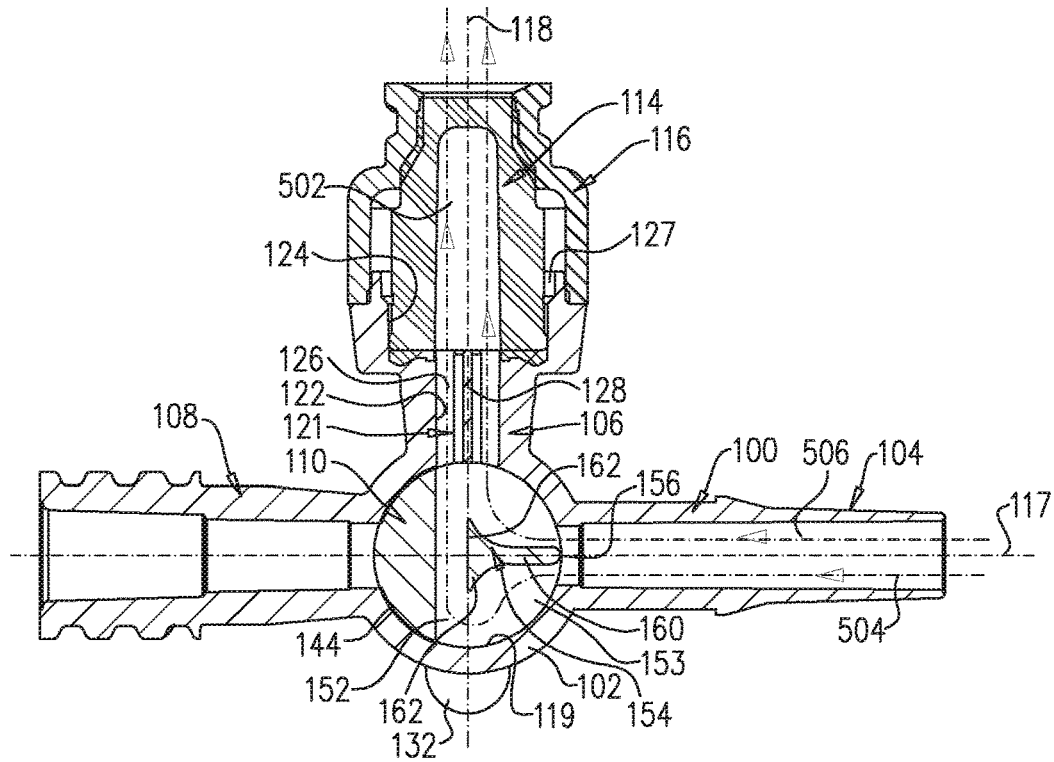

FIGS. 19B and 20B illustrate a second operating position of the stopcock of FIG. 1, where the handle element 110 is rotatably disposed within the main tubular portion 102 of the housing element 100, such that finger engageable protrusion 134 is aligned with port 108 of the housing element 100 and extends along an axis, which is parallel to axis 117.

FIGS. 19B and 20B illustrate a second operating position of the stopcock of FIG. 1, which is typically employed for drawing blood or other fluids from the patient. The user typically connects a syringe to port 106, such that the luer of the syringe penetrates elastomeric element 114, such that the luer of the syringe communicates with an internal volume 502 of the elastomeric element 114, and draws blood from the patient through port 104, via bore 152 as indicated by an arrow 504 and via recess 153 as indicated by an arrow 506, through port 106 to the syringe. It is appreciated that this operating position may also be used for supplying a medicament to the patient when port 108 is closed, in a flow direction opposite to that indicated by arrows 504 and 506.

It is particularly noted that in this operating position, a portion of fluid from port 104 enters the first fluid flow passage, defined by side-to-side bore 152. This portion of fluid flows along a portion of the second fluid flow passage, specifically along one side of the flat wall 160 and thereafter first concave portion 162 of the fluid flow guide 154, the fluid is then directed into side-to-side bore 152 and then in turn flows along side-to-side bore 152 into cylindrical bore 122 of port 106 and through the interior volume 502 of the elastomeric element 114 into the syringe, which is connected to port 106.

It is further particularly noted that the remaining portion of fluid from port 104 enters the second fluid flow passage, which is preferably defined by the circumferential recess 153, such that in this operating position, the fluid flows along another side of flat wall 160 and thereafter along the second concave portion 162 of the fluid flow guide 154, which effectively directs the flow into cylindrical bore 122 of port 106, and further into the internal volume 502 of the elastomeric element 114 and into the syringe, which is connected to port 106.

It is a particular feature of an embodiment of the present invention that the second fluid flow passage has various configurations in accordance with the configuration of the fluid flow guide 154. When the fluid flows along the flat wall 160 and the concave portions 162 of the fluid flow guide 154, a smooth laminar flow of liquid is provided and singularity points along the fluid flow passage are prevented.

It is appreciated that fluid flow rate increase is enabled by provision of the first fluid flow passage via bore 152 in addition to the second fluid flow passage defined by recess 153, while flushing characteristics of the stopcock due to the presence of fluid flow guides 154 and 128 are not compromised.

Figure 19C:
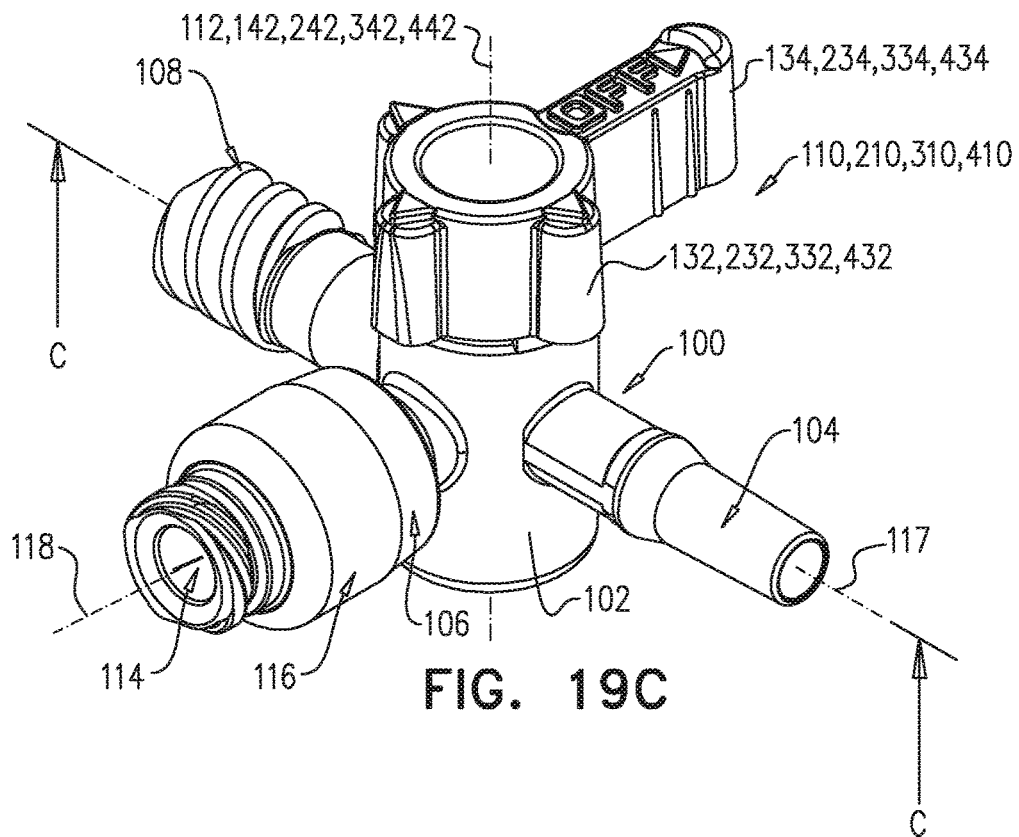
Figure 20C:
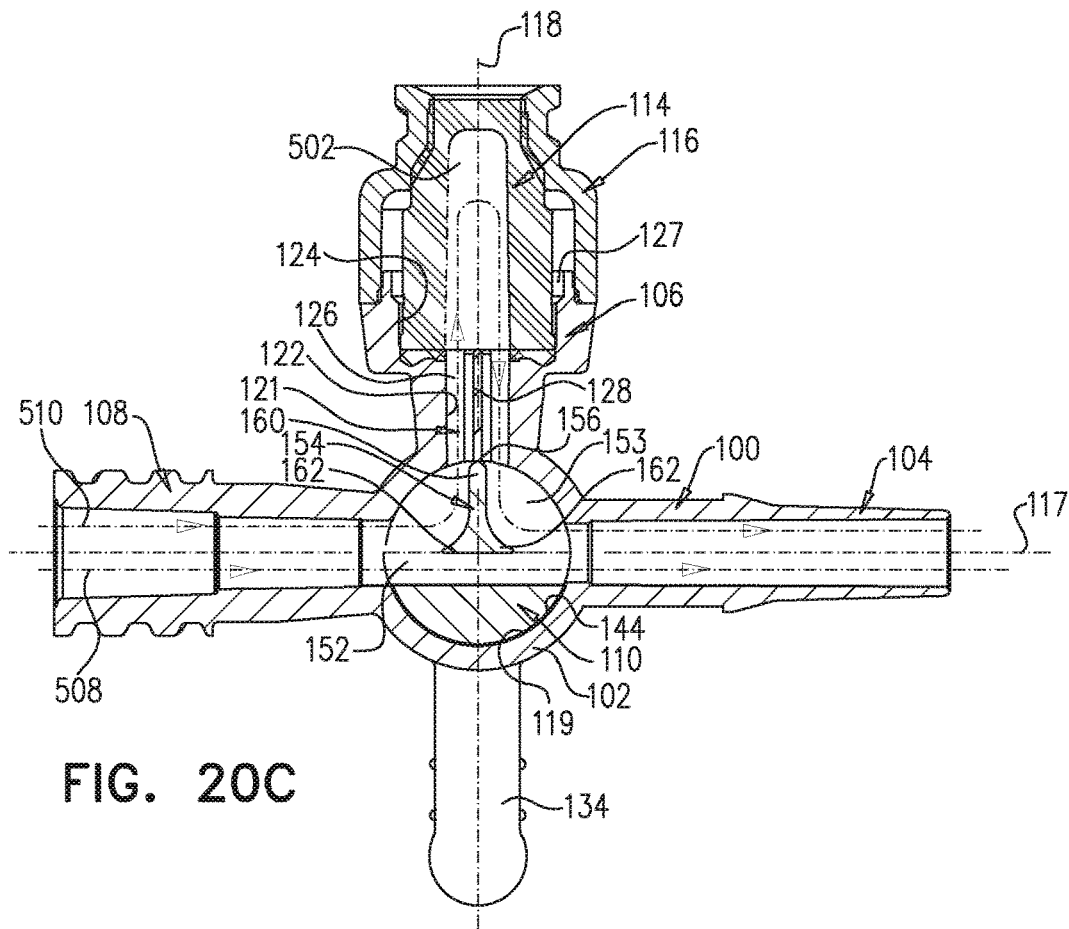

FIGS. 19C and 20C illustrate a third operating position of the stopcock of FIG. 1, where the handle element 110 is rotatably disposed within the main tubular portion 102 of the housing element 100, such that finger engageable protrusion 134 extends in a direction opposite to port 106 of the housing element 100 and extends along an axis, which is parallel to axis 118.

FIGS. 19C and 20C illustrate a third operating position of the stopcock of FIG. 1, which is typically employed for supplying a liquid to the patient from port 108 to port 104. Liquid flows via the first fluid flow passage from port 108 via bore 152 and into port 104, as indicated by an arrow 508. Liquid also simultaneously flows via the second fluid flow passage from port 108 via recess 153, around fluid flow guide 154 into interior volume 121 of port 106 and thereafter around fluid flow guide 128 into internal volume 502 of the elastomeric element 114, thereby flushing residual liquid therefrom, and flowing further around fluid flow guides 128 and 154 into port 104 and to the patient, as indicated by an arrow 510.

It is particularly noted that in this operating position, a portion of fluid from port 108 enters the first fluid flow passage, defined by side-to-side bore 152. This portion of fluid flows entirely along side-to-side bore 152 and into port 104.

It is particularly noted that the remaining portion of the fluid from port 108 enters the second fluid flow passage, which is preferably defined by the circumferential recess 153, such that in this operating position, the fluid flows along the first concave portion 162 and thereafter along one side of flat wall 160 of the fluid flow guide 154, which effectively directs the entire fluid flow that enters the second fluid flow passage into cylindrical bore 122 of port 106. Further, due to the presence of fluid flow guide 128 within port 106, the fluid is directed along one side of the fluid flow guide 128 into the internal volume 502 of the elastomeric element 114 and while flushing this internal volume, the fluid is directed along the other side of fluid flow guide 128, thereafter along the other side of flat wall 160 and the second concave portion 162 of the fluid flow guide 154 and eventually into port 104, as indicated by arrow 510.

It is a particular feature of an embodiment of the present invention that the second fluid flow passage has various configurations in accordance with the configuration of the fluid flow guide 154. When the fluid flows along the flat wall 160 and the concave portions 162 of the fluid flow guide 154, a smooth laminar flow of liquid is provided and singularity points along the fluid flow passage are prevented.

It is a particular feature of the present invention that the provision of fluid flow guides 154 and 128 generally overcomes problems of the presence of residual liquids remaining in the internal volume 121 of port 106 as well as in internal volume 502 of the elastomeric element 114. This is important in various therapeutic situations. For example when blood is drawn from the patient through port 106, there remains residual blood in the internal volume 121 of port 106 and the internal volume 502 of the elastomeric element 114. This blood, if left in internal volumes 121 and 502 for a period of time, can clot and thus become dangerous if delivered to the patient. In addition, the coagulated blood could occlude the liquid passageway extending through port 106. Various infections could possibly arise as a result of the retained blood.

This feature is also useful when a medicament is supplied to a patient through port 106. If a portion of the medicament remains in the internal volumes 121 of port 106 and 502 of the elastomeric element 114, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament from the internal volumes 121 and 502 and typically returning it to the patient without requiring the use of extra syringes and the opening of the medical set to the atmosphere, thereby increasing the chance of contamination.

It is an additional particular feature of an embodiment of the present invention that first fluid flow passage through side-to-side bore 152 is provided for increasing the flow rate through the stopcock of FIG. 1 while maintaining the flushing feature of volumes 121 and 502 via the second fluid flow passage.

Figure 19D:
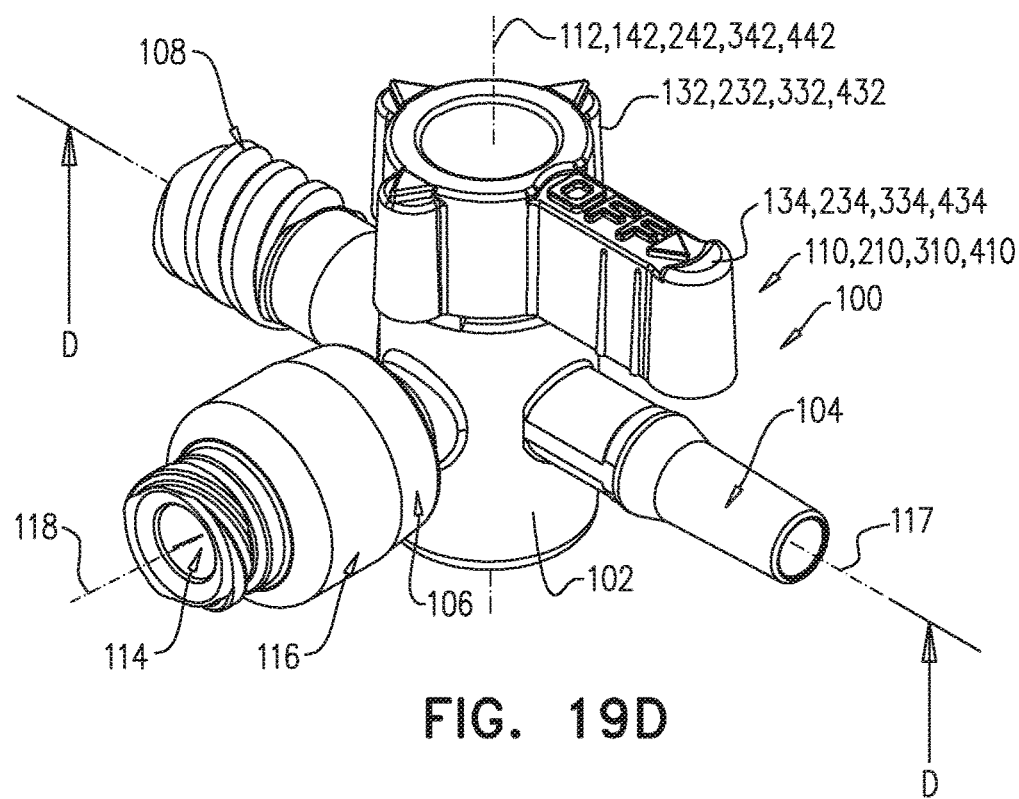
Figure 20D:
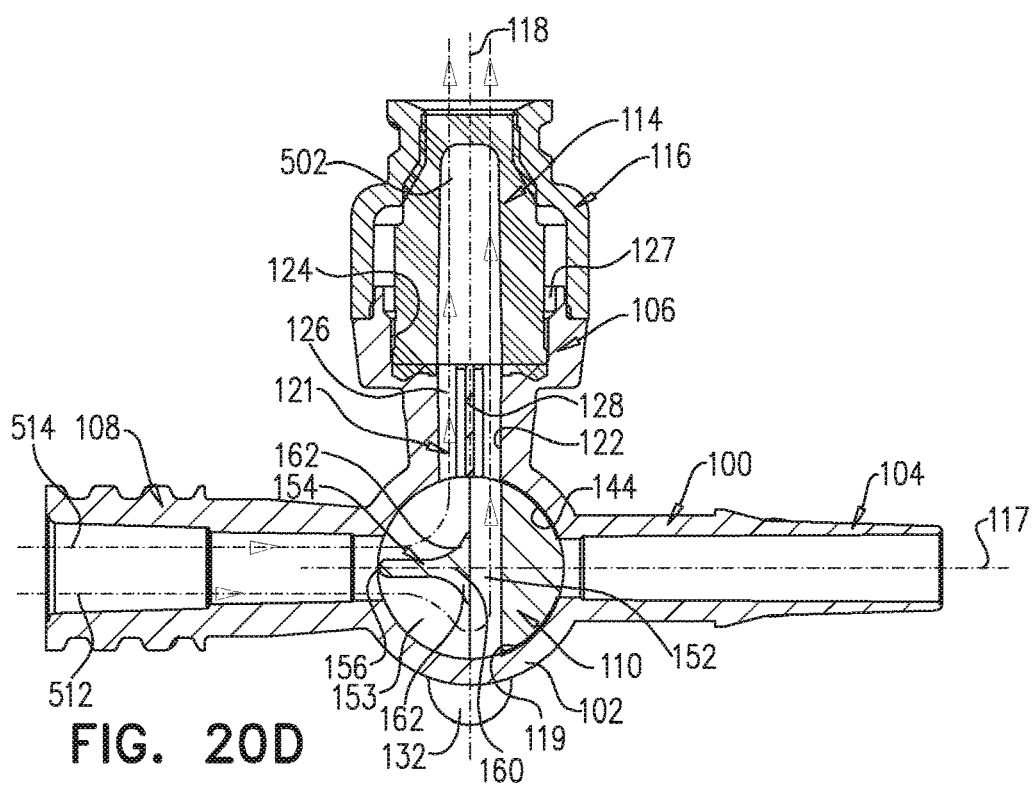

FIGS. 19D and 20D illustrate a fourth operating position of the stopcock of FIG. 1, where the handle element 110 is rotatably disposed within the main tubular portion 102 of the housing element 100, such that finger engageable protrusion 134 is aligned with port 104 of the housing element 100 and extends along an axis, which is parallel to axis 117.

FIGS. 19D and 20D illustrate a fourth operating position of the stopcock of FIG. 1, which may be used for flushing the IV set upstream of the stopcock, when port 106 is open to the atmosphere as by insertion of a male luer connector, such as a syringe tip (not shown), into the elastomeric element 114 of the valve thereof. The insertion of the male luer connector activates the flow of liquid from port 108 via the first fluid flow through bore 152 and into port 106, as indicated by an arrow 512. Liquid also simultaneously flows via the second fluid flow passage from port 108 via recess 153, around fluid flow guide 154 into interior volume 121 of port 106 and thereafter around fluid flow guide 128 into internal volume 502 of the elastomeric element 114, flushing residual liquid therefrom, via port 106 to the IV line, as indicated by an arrow 514.

It is particularly noted that in this operating position, a portion of fluid from port 108 enters the first fluid flow passage, defined by side-to-side bore 152. This portion of fluid flows along a portion of the second fluid flow passage, specifically along one side of the flat wall 160 and thereafter first concave portion 162 of the fluid flow guide 154, the fluid is then directed into side-to-side bore 152 and then in turn flows along side-to-side bore 152 into cylindrical bore 122 of port 106 and through the interior volume 502 of the elastomeric element 114 into the syringe, which is connected to port 106.

It is particularly noted that the remaining portion of fluid from port 108 enters the second fluid flow passage, which is preferably defined by the circumferential recess 153, such that in this operating position, the fluid flows along another side of flat wall 160 and thereafter the second concave portion 162 of the fluid flow guide 154, which effectively directs the flow into cylindrical bore 122 of port 106, and further into the internal volume 502 of the elastomeric element 114 and into the syringe, which is connected to port 106.

It is a particular feature of an embodiment of the present invention that the second fluid flow passage has various configurations in accordance with the configuration of the fluid flow guide 154. When the fluid flows along the flat wall 160 and the concave portions 162 of the fluid flow guide 154, a smooth laminar flow of liquid is provided and singularity points along the fluid flow passage are prevented.

Alternatively, this operating position may be employed for pushing liquid via the side port 106, through port 108, in a direction opposite arrows 512 and 514, for uses such as mixing liquid in the pressure bag.

It is appreciated that fluid flow rate increase is enabled by provision of the first fluid flow passage via bore 152 in addition to the second fluid flow passage defined by recess 153, while flushing characteristics of the stopcock due to the presence of fluid flow guides 154 and 128 are not compromised.

References is now made to FIGS. 19A, 19B, 19C and 19D, which are simplified assembled pictorial illustrations of the stopcock of FIG. 7 in four operative orientations and to FIGS. 21A, 21B, 21C and 21D, which are sectional illustrations of the stopcock having the handle shown in FIGS. 8A-10C, taken along section lines A-A, B-B, C-C and D-D in FIGS. 19A, 19B, 19C and 19D respectively.

Figure 21A:
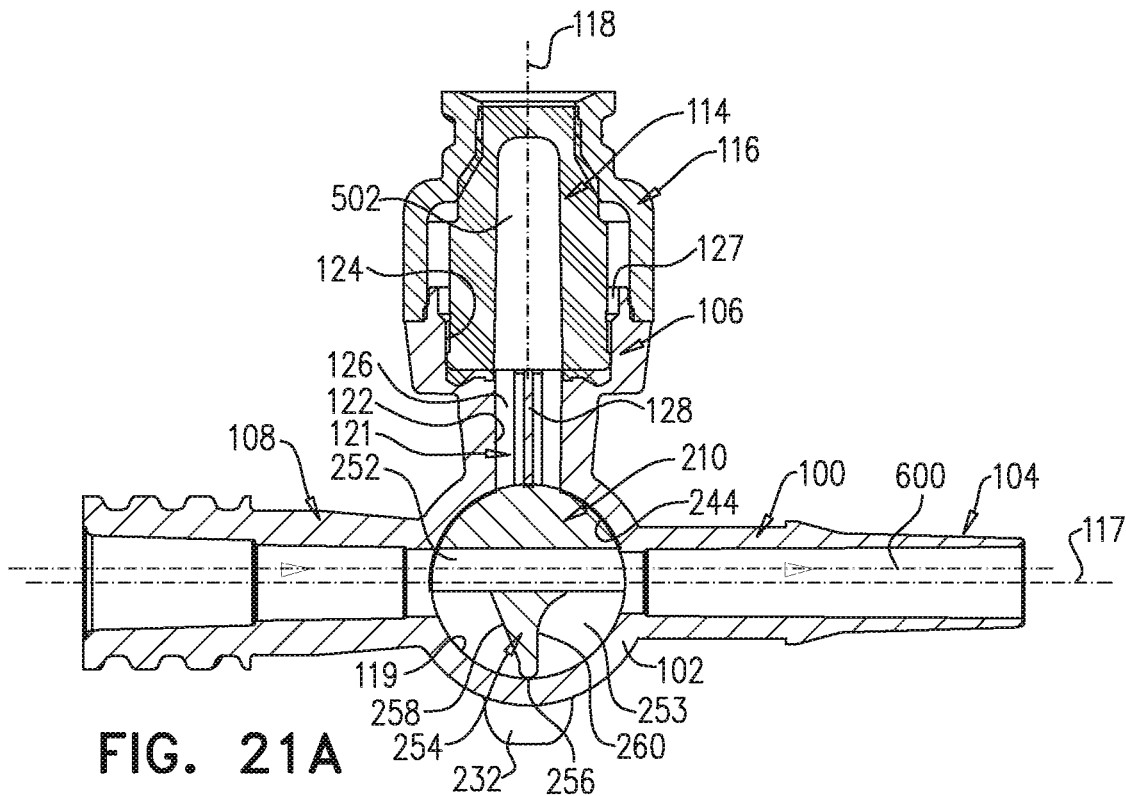
FIGS. 21A, 21B, 21C and 21D are sectional illustrations of a stopcock having the handle shown in FIGS. 8A-10C, taken along section lines A-A, B-B, C-C and D-D in FIGS. 19A, 19B, 19C and 19D respectively.

FIGS. 19A and 21A illustrate a first operating position of the stopcock of FIG. 7, which is typically employed for blood pressure monitoring by means of a pressure transducer, where there should be no contact of fluid with the elastomeric element 114. In this first operating position, the handle element 210 is rotatably disposed within the main tubular portion 102 of the housing element 100, such that finger engageable protrusion 234 is aligned with port 106 of the housing element 100 and extends along an axis, which is parallel to axis 118.

As seen in FIG. 21A, there is a fluid communication between ports 104 and 108 through first fluid flow passage defined by side-to-side extending bore 252, as indicated by an arrow 600. Liquid communication from port 108 to port 104 through second fluid flow passage, defined by recess 253, past fluid flow guide 254 is prevented, because it is blocked by fluid flow guide 254, whose edge 256 sealingly engages an inner facing wall of central bore 119 of housing element 100. This orientation may be utilized to provide fluid flow between ports 104 and 108 only.

It is appreciated that first fluid flow passage allows liquid communication between port 104 and 108 and liquid communication along the second fluid flow passage, particularly along recess 253, in this orientation is preferably blocked.

Alternatively, in accordance with another embodiment of the present invention, the fluid flow guide 254 can extend toward the inner facing wall of central bore 119 of housing element 100, whereas the edge 256 is slightly spaced therefrom in order to allow minimal fluid flow passage through the second fluid flow passage, along recess 253 and around fluid flow guide 254.

It is noted that liquid communication between port 104 and 108 through side-to-side bore 252 is sufficient for the purpose of pressure monitoring, while avoiding dampening of the signal, which could have occurred if the fluid would come in contact with elastomeric element 114.

FIGS. 19B and 20B illustrate a second operating position of the stopcock of FIG. 7, where the handle element 210 is rotatably disposed within the main tubular portion 102 of the housing element 100, such that finger engageable protrusion 234 is aligned with port 108 of the housing element 100 and extends along an axis, which is parallel to axis 117.

Figure 21B:
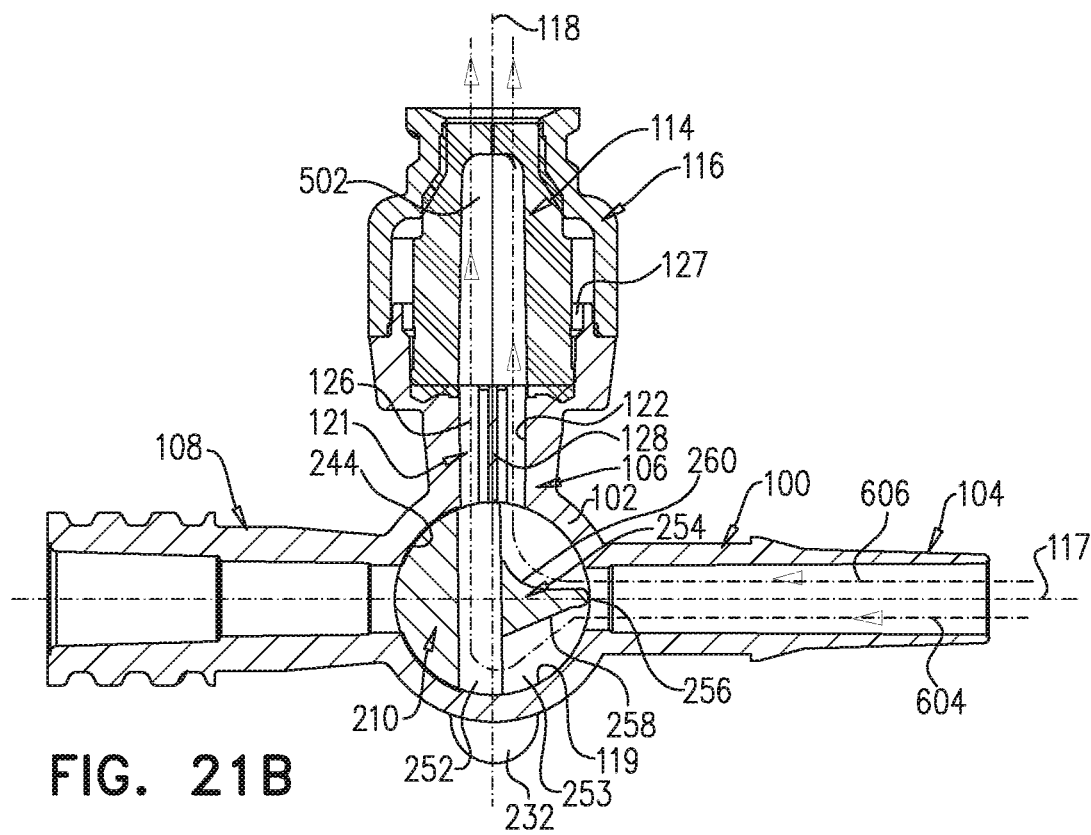

FIGS. 19B and 21B illustrate a second operating position of the stopcock of FIG. 7, which is typically employed for drawing blood or other fluids from the patient. The user typically connects a syringe to port 106, such that the luer of the syringe penetrates elastomeric element 114, such that the luer of the syringe communicates with an internal volume 502 of the elastomeric element 114, and draws blood from the patient through port 104, via bore 252 as indicated by an arrow 604 and via recess 253 as indicated by an arrow 606, through port 106 to the syringe. It is appreciated that this operating position may also be used for supplying a medicament to the patient when port 108 is closed, in a flow direction opposite to that indicated by arrows 604 and 606.

It is particularly noted that in this operating position, a portion of fluid from port 104 enters the first fluid flow passage, defined by side-to-side bore 252. This portion of fluid flows along a portion of the second fluid flow passage, specifically along inclined wall surface 258 of the fluid flow guide 254, the fluid is then directed into side-to-side bore 252 and then in turn flows along side-to-side bore 252 into cylindrical bore 122 of port 106 and through the interior volume 502 of the elastomeric element 114 into the syringe, which is connected to port 106.

It is further particularly noted that the remaining portion of fluid from port 104 enters the second fluid flow passage, which is preferably defined by the circumferential recess 253, such that in this operating position, the fluid flows along concave wall surface 260 of the fluid flow guide 254, which effectively directs the flow into cylindrical bore 122 of port 106, and further into the internal volume 502 of the elastomeric element 114 and into the syringe, which is connected to port 106.

It is a particular feature of an embodiment of the present invention that the second fluid flow passage has various configurations in accordance with the configuration of the fluid flow guide 254. When the fluid flows along inclined wall surface 258 of the fluid flow guide 254, a smooth laminar flow of liquid is provided and singularity points along the fluid flow passage are prevented.

It is appreciated that fluid flow rate increase is enabled by provision of the first fluid flow passage via bore 252 in addition to the second fluid flow passage defined by recess 253, while flushing characteristics of the stopcock due to the presence of fluid flow guides 254 and 128 are not compromised.

Figure 21C:
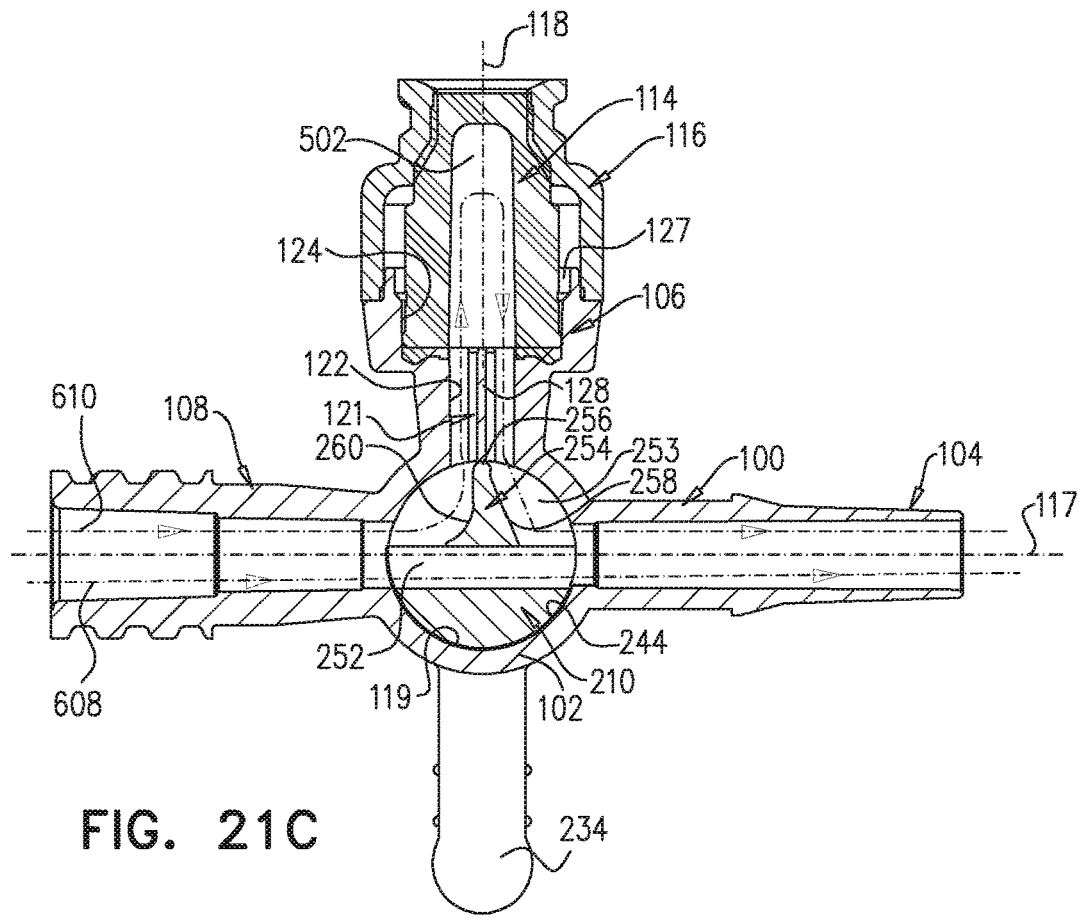

FIGS. 19C and 21C illustrate a third operating position of the stopcock of FIG. 7, where the handle element 210 is rotatably disposed within the main tubular portion 102 of the housing element 100, such that finger engageable protrusion 234 extends in a direction opposite to port 106 of the housing element 100 and extends along an axis, which is parallel to axis 118.

FIGS. 19C and 21C illustrate a third operating position of the stopcock of FIG. 7, which is typically employed for supplying a liquid to the patient from port 108 to port 104. Liquid flows via the first fluid flow passage from port 108 via bore 252 and into port 104, as indicated by an arrow 608. Liquid also simultaneously flows via the second fluid flow passage from port 108 via recess 253, around fluid flow guide 254 into interior volume 121 of port 106 and thereafter around fluid flow guide 128 into internal volume 502 of the elastomeric element 114, thereby flushing residual liquid therefrom, and flowing further around fluid flow guides 128 and 254 into port 104 and to the patient, as indicated by an arrow 610.

It is particularly noted that in this operating position, a portion of fluid from port 108 enters the first fluid flow passage, defined by side-to-side bore 252. This portion of fluid flows entirely along side-to-side bore 252 and into port 104.

It is particularly noted that the remaining portion of the fluid from port 108 enters the second fluid flow passage, which is preferably defined by the circumferential recess 253, such that in this operating position, the fluid flows along concave wall surface 260 of the fluid flow guide 254, which effectively directs the entire fluid flow that enters the second fluid flow passage into cylindrical bore 122 of port 106. Further, due to the presence of fluid flow guide 128 within port 106, the fluid is directed along one side of the fluid flow guide 128 into the internal volume 502 of the elastomeric element 114 and while flushing this internal volume, the fluid is directed along the other side of fluid flow guide 128, thereafter along inclined wall surface 258 of the fluid flow guide 254 and eventually into port 104, as indicated by arrow 610.

It is a particular feature of an embodiment of the present invention that the second fluid flow passage has various configurations in accordance with the configuration of the fluid flow guide 254. When the fluid flows along the concave wall surface 260 and along inclined wall surface 158 of the fluid flow guide 254, a smooth laminar flow of liquid is provided and singularity points along the fluid flow passage are prevented.

It is a particular feature of the present invention that the provision of fluid flow guides 254 and 128 generally overcomes problems of the presence of residual liquids remaining in the internal volume 121 of port 106 as well as in internal volume 502 of the elastomeric element 114. This is important in various therapeutic situations. For example, when blood is drawn from the patient through port 106, there remains residual blood in the internal volume 121 of port 106 and the internal volume 502 of the elastomeric element 114. This blood, if left in internal volumes 121 and 502 for a period of time, can clot and thus become dangerous if delivered to the patient. In addition, the coagulated blood could occlude the liquid passageway extending through port 106. Various infections could possibly arise as a result of the retained blood.

This feature is also useful when a medicament is supplied to a patient through port 106. If a portion of the medicament remains in the internal volumes 121 of port 106 and 502 of the elastomeric element 114, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament from the internal volumes 121 and 502 and typically returning it to the patient without requiring the use of extra syringes and the opening of the medical set to the atmosphere, thereby increasing the chance of contamination.

It is an additional particular feature of an embodiment of the present invention that first fluid flow passage through side-to-side bore 252 is provided for increasing the flow rate through the stopcock of FIG. 7 while maintaining the flushing feature of volumes 121 and 502 via the second fluid flow passage.

Figure 21D:
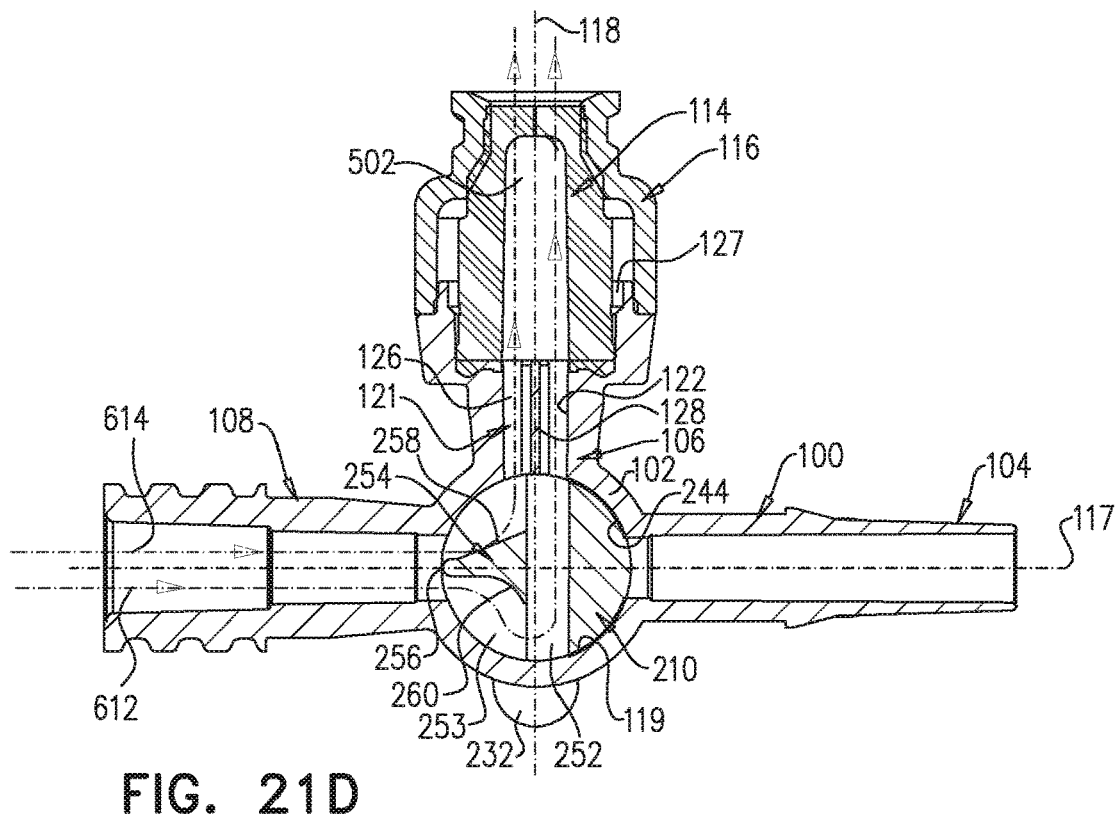

FIGS. 19D and 21D illustrate a fourth operating position of the stopcock of FIG. 7, where the handle element 210 is rotatably disposed within the main tubular portion 102 of the housing element 100, such that finger engageable protrusion 234 is aligned with port 104 of the housing element 100 and extends along an axis, which is parallel to axis 117.

FIGS. 19D and 21D illustrate a fourth operating position of the stopcock of FIG. 7, which may be used for flushing the IV set upstream of the stopcock, when port 106 is open to the atmosphere as by insertion of a male luer connector, such as a syringe tip (not shown), into the elastomeric element 114 of the valve thereof. The insertion of the male luer connector activates the flow of liquid from port 108 via the first fluid flow through bore 252 and into port 106, as indicated by an arrow 612. Liquid also simultaneously flows via the second fluid flow passage from port 108 via recess 253, around fluid flow guide 254 into interior volume 121 of port 106 and thereafter around fluid flow guide 128 into internal volume 502 of the elastomeric element 114, flushing residual liquid therefrom, via port 106 to the IV line, as indicated by an arrow 614.

It is particularly noted that in this operating position, a portion of fluid from port 108 enters the first fluid flow passage, defined by side-to-side bore 252. This portion of fluid flows along a portion of the second fluid flow passage, specifically along concave wall surface 260 of the fluid flow guide 254, the fluid is then directed into side-to-side bore 252 and then in turn flows along side-to-side bore 252 into cylindrical bore 122 of port 106 and through the interior volume 502 of the elastomeric element 114 into the syringe, which is connected to port 106.

It is particularly noted that the remaining portion of fluid from port 108 enters the second fluid flow passage, which is preferably defined by the circumferential recess 253, such that in this operating position, the fluid flows along inclined wall surface 258 of the fluid flow guide 254, which effectively directs the flow into cylindrical bore 122 of port 106, and further into the internal volume 502 of the elastomeric element 114 and into the syringe, which is connected to port 106.

It is a particular feature of an embodiment of the present invention that the second fluid flow passage has various configurations in accordance with the configuration of the fluid flow guide 254. When the fluid flows along the concave wall surface 260 of the fluid flow guide 254, a smooth laminar flow of liquid is provided and singularity points along the fluid flow passage are prevented.

Alternatively, this operating position may be employed for pushing liquid via the side port 106, through port 108, in a direction opposite arrows 612 and 614, for uses such as mixing liquid in the pressure bag.

It is appreciated that fluid flow rate increase is enabled by provision of the first fluid flow passage via bore 252 in addition to the second fluid flow passage defined by recess 253, while flushing characteristics of the stopcock due to the presence of fluid flow guides 254 and 128 are not compromised.

References is now made to FIGS. 19A, 19B, 19C and 19D, which are simplified assembled pictorial illustrations of the stopcock of FIG. 11 in four operative orientations and to FIGS. 22A, 22B, 22C and 22D, which are sectional illustrations of the stopcock having the handle shown in FIGS. 12A-14C, taken along section lines A-A, B-B, C-C and D-D in FIGS. 19A, 19B, 19C and 19D respectively.

Figure 22A:
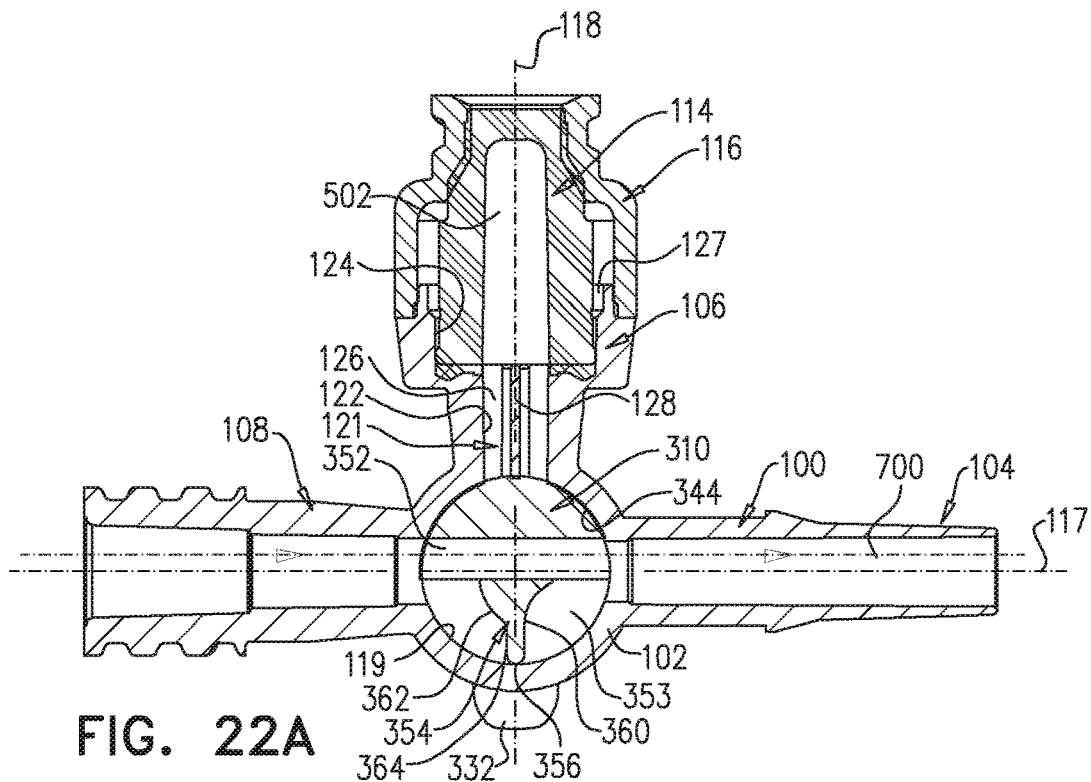
FIGS. 22A, 22B, 22C and 22D are sectional illustrations of a stopcock having the handle shown in FIGS. 12A-14C, taken along section lines A-A, B-B, C-C and D-D in FIGS. 19A, 19B, 19C and 19D respectively.

FIGS. 19A and 22A illustrate a first operating position of the stopcock of FIG. 11, which is typically employed for blood pressure monitoring by means of a pressure transducer, where there should be no contact of fluid with the elastomeric element 114. In this first operating position, the handle element 310 is rotatably disposed within the main tubular portion 102 of the housing element 100, such that finger engageable protrusion 334 is aligned with port 106 of the housing element 100 and extends along an axis, which is parallel to axis 118.

As seen in FIG. 22A, there is a fluid communication between ports 104 and 108 through first fluid flow passage defined by side-to-side extending bore 352, as indicated by an arrow 700. Liquid communication from port 108 to port 104 through second fluid flow passage, defined by recess 353, past fluid flow guide 354 is prevented, because it is blocked by fluid flow guide 354, whose edge 356 sealingly engages an inner facing wall of central bore 119 of housing element 100. This orientation may be utilized to provide fluid flow between ports 104 and 108 only.

It is appreciated that first fluid flow passage allows liquid communication between port 104 and 108 and liquid communication along the second fluid flow passage, particularly along recess 353, in this orientation is preferably blocked.

Alternatively, in accordance with another embodiment of the present invention, the fluid flow guide 354 can extend toward the inner facing wall of central bore 119 of housing element 100, whereas the edge 356 is slightly spaced therefrom in order to allow minimal fluid flow passage through the second fluid flow passage, along recess 353 and around fluid flow guide 354.

It is noted that liquid communication between port 104 and 108 through side-to-side bore 352 is sufficient for the purpose of pressure monitoring, while avoiding dampening of the signal, which could have occurred if the fluid would come in contact with elastomeric element 114.

Figure 22B:
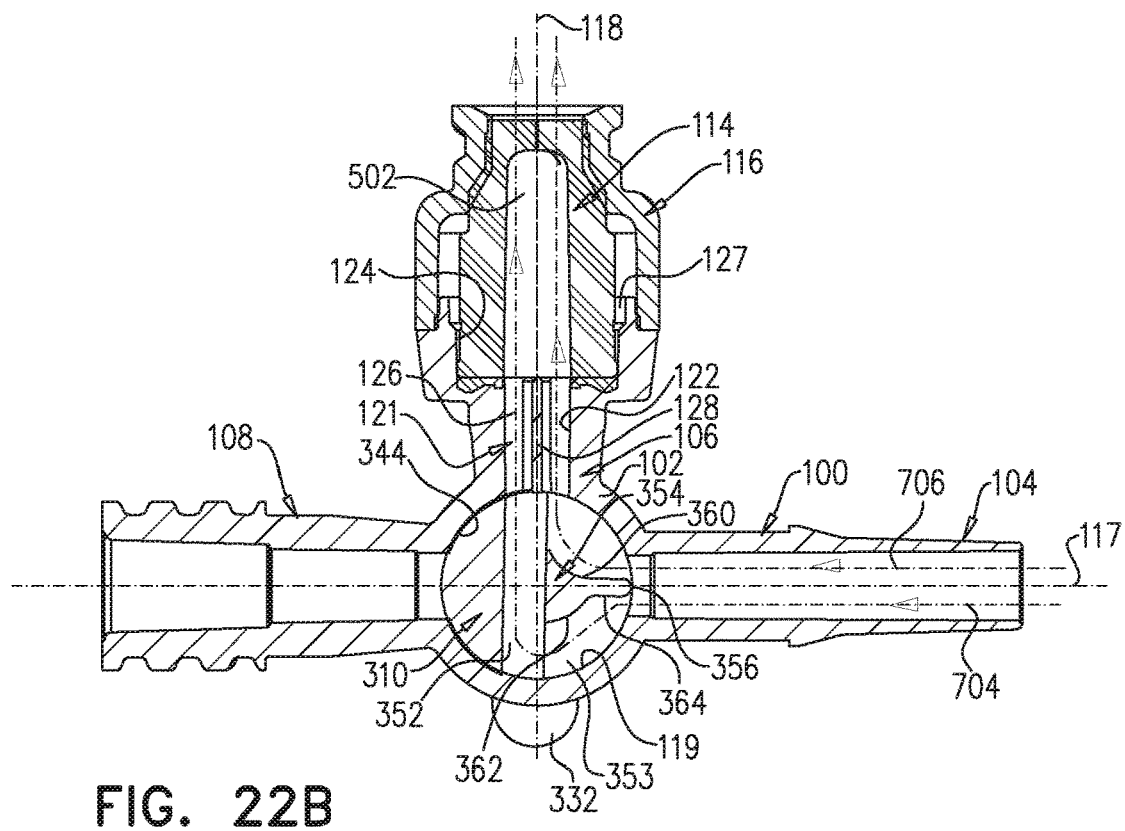

FIGS. 19B and 22B illustrate a second operating position of the stopcock of FIG. 11, where the handle element 310 is rotatably disposed within the main tubular portion 102 of the housing element 100, such that finger engageable protrusion 334 is aligned with port 108 of the housing element 100 and extends along an axis, which is parallel to axis 117.

FIGS. 19B and 22B illustrate a second operating position of the stopcock of FIG. 11, which is typically employed for drawing blood or other fluids from the patient. The user typically connects a syringe to port 106, such that the luer of the syringe penetrates elastomeric element 114, such that the luer of the syringe communicates with an internal volume 502 of the elastomeric element 114, and draws blood from the patient through port 104, via bore 352 as indicated by an arrow 704 and via recess 353 as indicated by an arrow 706, through port 106 to the syringe. It is appreciated that this operating position may also be used for supplying a medicament to the patient when port 108 is closed, in a flow direction opposite to that indicated by arrows 704 and 706.

It is particularly noted that in this operating position, a portion of fluid from port 104 enters the first fluid flow passage, defined by side-to-side bore 352. This portion of fluid flows along a portion of the second fluid flow passage, specifically along straight wall surface 364 and thereafter convex wall surface 362 of the fluid flow guide 354, the fluid is then directed into side-to-side bore 352 and then in turn flows along side-to-side bore 352 into cylindrical bore 122 of port 106 and through the interior volume 502 of the elastomeric element 114 into the syringe, which is connected to port 106.

It is further particularly noted that the remaining portion of fluid from port 104 enters the second fluid flow passage, which is preferably defined by the circumferential recess 353, such that in this operating position, the fluid flows along concave wall surface 360 of the fluid flow guide 354, which effectively directs the flow into cylindrical bore 122 of port 106, and further into the internal volume 502 of the elastomeric element 114 and into the syringe, which is connected to port 106.

It is a particular feature of an embodiment of the present invention that the second fluid flow passage has various configurations in accordance with the configuration of the fluid flow guide 354. When the fluid flows along straight wall surface 364 and thereafter convex wall surface 362 of the fluid flow guide 354, a smooth laminar flow of liquid is provided and singularity points along the fluid flow passage are prevented.

It is appreciated that fluid flow rate increase is enabled by provision of the first fluid flow passage via bore 352 in addition to the second fluid flow passage defined by recess 353, while flushing characteristics of the stopcock due to the presence of fluid flow guides 354 and 128 are not compromised.

Figure 22C:
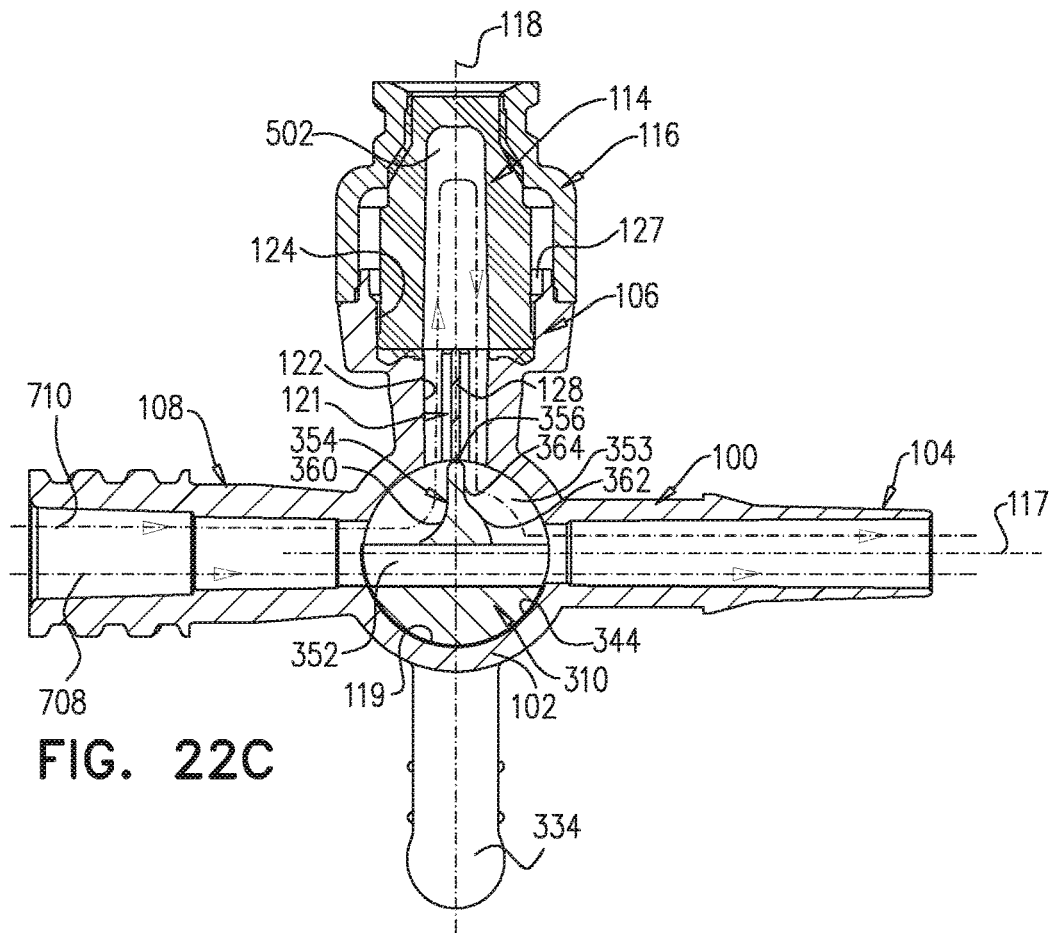

FIGS. 19C and 22C illustrate a third operating position of the stopcock of FIG. 11, where the handle element 310 is rotatably disposed within the main tubular portion 102 of the housing element 100, such that finger engageable protrusion 334 extends in a direction opposite to port 106 of the housing element 100 and extends along an axis, which is parallel to axis 118.

FIGS. 19C and 22C illustrate a third operating position of the stopcock of FIG. 11, which is typically employed for supplying a liquid to the patient from port 108 to port 104. Liquid flows via the first fluid flow passage from port 108 via bore 352 and into port 104, as indicated by an arrow 708. Liquid also simultaneously flows via the second fluid flow passage from port 108 via recess 353, around fluid flow guide 354 into interior volume 121 of port 106 and thereafter around fluid flow guide 128 into internal volume 502 of the elastomeric element 114, thereby flushing residual liquid therefrom, and flowing further around fluid flow guides 128 and 354 into port 104 and to the patient, as indicated by an arrow 710.

It is particularly noted that in this operating position, a portion of fluid from port 108 enters the first fluid flow passage, defined by side-to-side bore 352. This portion of fluid flows entirely along side-to-side bore 352 and into port 104.

It is particularly noted that the remaining portion of the fluid from port 108 enters the second fluid flow passage, which is preferably defined by the circumferential recess 353, such that in this operating position, the fluid flows along concave wall surface 360 of the fluid flow guide 354, which effectively directs the entire fluid flow that enters the second fluid flow passage into cylindrical bore 122 of port 106. Further, due to the presence of fluid flow guide 128 within port 106, the fluid is directed along one side of the fluid flow guide 128 into the internal volume 502 of the elastomeric element 114 and while flushing this internal volume, the fluid is directed along the other side of fluid flow guide 128, thereafter along straight wall surface 364 and convex wall surface 362 of the fluid flow guide 354 and eventually into port 104, as indicated by arrow 710.

It is a particular feature of an embodiment of the present invention that the second fluid flow passage has various configurations in accordance with the configuration of the fluid flow guide 354. When the fluid flows along concave wall surface 360 and then straight wall surface 364 and thereafter convex wall surface 362 of the fluid flow guide 354, a smooth laminar flow of liquid is provided and singularity points along the fluid flow passage are prevented.

It is a particular feature of the present invention that the provision of fluid flow guides 354 and 128 generally overcomes problems of the presence of residual liquids remaining in the internal volume 121 of port 106 as well as in internal volume 502 of the elastomeric element 114. This is important in various therapeutic situations. For example, when blood is drawn from the patient through port 106, there remains residual blood in the internal volume 121 of port 106 and the internal volume 502 of the elastomeric element 114. This blood, if left in internal volumes 121 and 502 for a period of time, can clot and thus become dangerous if delivered to the patient. In addition, the coagulated blood could occlude the liquid passageway extending through port 106. Various infections could possibly arise as a result of the retained blood.

This feature is also useful when a medicament is supplied to a patient through port 106. If a portion of the medicament remains in the internal volumes 121 of port 106 and 502 of the elastomeric element 114, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament from the internal volumes 121 and 502 and typically returning it to the patient without requiring the use of extra syringes and the opening of the medical set to the atmosphere, thereby increasing the chance of contamination.

It is an additional particular feature of an embodiment of the present invention that first fluid flow passage through side-to-side bore 352 is provided for increasing the flow rate through the stopcock of FIG. 11 while maintaining the flushing feature of volumes 121 and 502 via the second fluid flow passage.

Figure 22D:
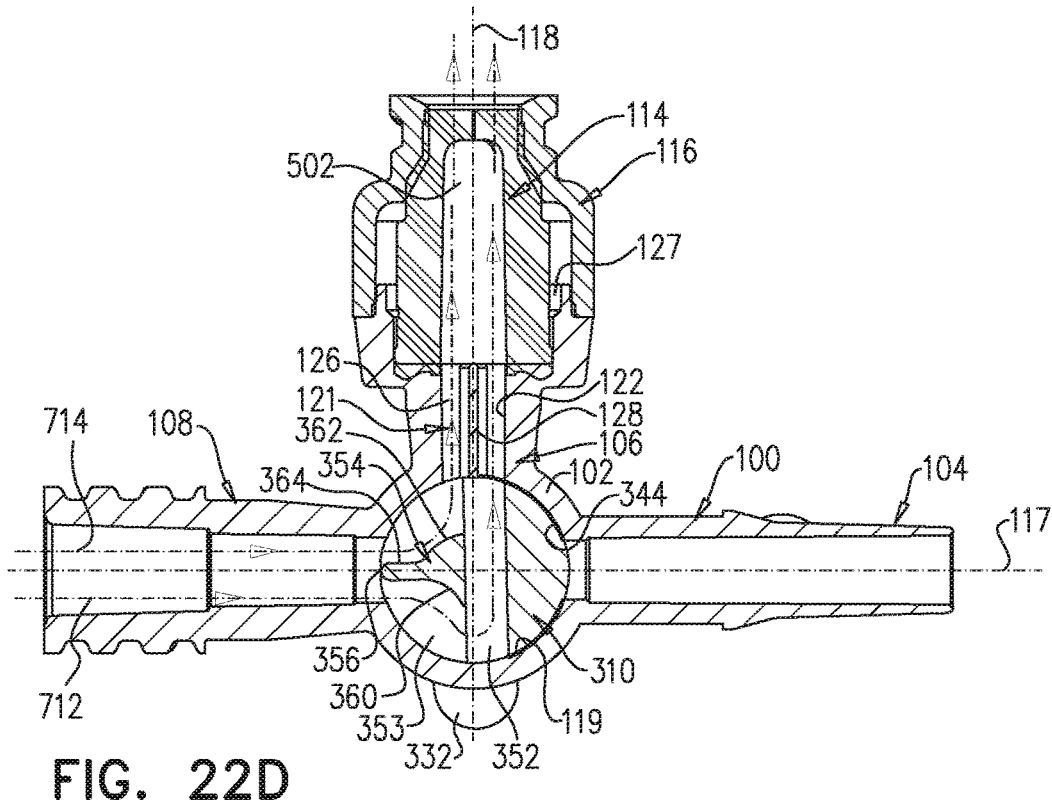

FIGS. 19D and 22D illustrate a fourth operating position of the stopcock of FIG. 11, where the handle element 310 is rotatably disposed within the main tubular portion 102 of the housing element 100, such that finger engageable protrusion 334 is aligned with port 104 of the housing element 100 and extends along an axis, which is parallel to axis 117.

FIGS. 19D and 22D illustrate a fourth operating position of the stopcock of FIG. 11, which may be used for flushing the IV set upstream of the stopcock, when port 106 is open to the atmosphere as by insertion of a male luer connector, such as a syringe tip (not shown), into the elastomeric element 114 of the valve thereof. The insertion of the male luer connector activates the flow of liquid from port 108 via the first fluid flow through bore 352 and into port 106, as indicated by an arrow 712. Liquid also simultaneously flows via the second fluid flow passage from port 108 via recess 353, around fluid flow guide 354 into interior volume 121 of port 106 and thereafter around fluid flow guide 128 into internal volume 502 of the elastomeric element 114, flushing residual liquid therefrom, via port 106 to the IV line, as indicated by an arrow 714.

It is particularly noted that in this operating position, a portion of fluid from port 108 enters the first fluid flow passage, defined by side-to-side bore 352. This portion of fluid flows along a portion of the second fluid flow passage, specifically along concave wall surface 360 of the fluid flow guide 354, the fluid is then directed into side-to-side bore 352 and then in turn flows along side-to-side bore 352 into cylindrical bore 122 of port 106 and through the interior volume 502 of the elastomeric element 114 into the syringe, which is connected to port 106.

It is particularly noted that the remaining portion of fluid from port 108 enters the second fluid flow passage, which is preferably defined by the circumferential recess 353, such that in this operating position, the fluid flows along straight wall surface 364 and convex wall surface 362 of the fluid flow guide 354, which effectively directs the flow into cylindrical bore 122 of port 106, and further into the internal volume 502 of the elastomeric element 114 and into the syringe, which is connected to port 106.

It is a particular feature of an embodiment of the present invention that the second fluid flow passage has various configurations in accordance with the configuration of the fluid flow guide 354. When the fluid flows along concave wall surface 360 of the fluid flow guide 354, a smooth laminar flow of liquid is provided and singularity points along the fluid flow passage are prevented.

Alternatively, this operating position may be employed for pushing liquid via the side port 106, through port 108, in a direction opposite arrows 712 and 714, for uses such as mixing liquid in the pressure bag.

It is appreciated that fluid flow rate increase is enabled by provision of the first fluid flow passage via bore 352 in addition to the second fluid flow passage defined by recess 353, while flushing characteristics of the stopcock due to the presence of fluid flow guides 354 and 128 are not compromised.

References is now made to FIGS. 19A, 19B, 19C and 19D, which are simplified assembled pictorial illustrations of the stopcock of FIG. 15 in four operative orientations and to FIGS. 23A, 23B, 23C and 23D, which are sectional illustrations of the stopcock having the handle shown in FIGS. 16A-18C, taken along section lines A-A, B-B, C-C and D-D in FIGS. 19A, 19B, 19C and 19D respectively.

Figure 23A:
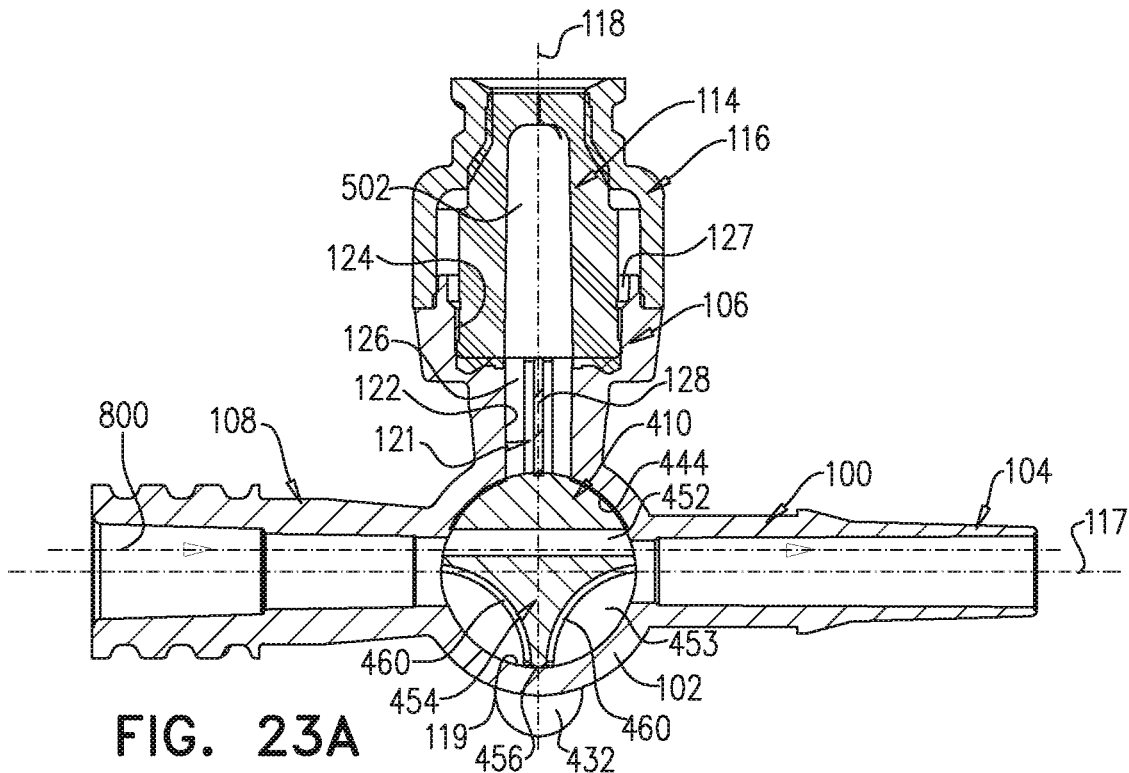
FIGS. 23A, 23B, 23C and 23D are sectional illustrations of a stopcock having the handle shown in FIGS. 16A-18C, taken along section lines A-A, B-B, C-C and D-D in FIGS. 19A, 19B, 19C and 19D respectively.

FIGS. 19A and 23A illustrate a first operating position of the stopcock of FIG. 15, which is typically employed for blood pressure monitoring by means of a pressure transducer, where there should be no contact of fluid with the elastomeric element 114. In this first operating position, the handle element 410 is rotatably disposed within the main tubular portion 102 of the housing element 100, such that finger engageable protrusion 434 is aligned with port 106 of the housing element 100 and extends along an axis, which is parallel to axis 118.

As seen in FIG. 23A, there is a fluid communication between ports 104 and 108 through first fluid flow passage defined by side-to-side extending bore 452, as indicated by an arrow 800. Liquid communication from port 108 to port 104 through second fluid flow passage, defined by recess 453, past fluid flow guide 454 is prevented, because it is blocked by fluid flow guide 454, whose edge 456 sealingly engages an inner facing wall of central bore 119 of housing element 100. This orientation may be utilized to provide fluid flow between ports 104 and 108 only.

It is appreciated that first fluid flow passage allows liquid communication between port 104 and 108 and liquid communication along the second fluid flow passage, particularly along recess 453, in this orientation is preferably blocked.

Alternatively, in accordance with another embodiment of the present invention, the fluid flow guide 454 can extend toward the inner facing wall of central bore 119 of housing element 100, whereas the edge 456 is slightly spaced therefrom in order to allow minimal fluid flow passage through the second fluid flow passage, along recess 453 and around fluid flow guide 454.

It is noted that liquid communication between port 104 and 108 through side-to-side bore 452 is sufficient for the purpose of pressure monitoring, while avoiding dampening of the signal, which could have occurred if the fluid would come in contact with elastomeric element 114.

Figure 23B:
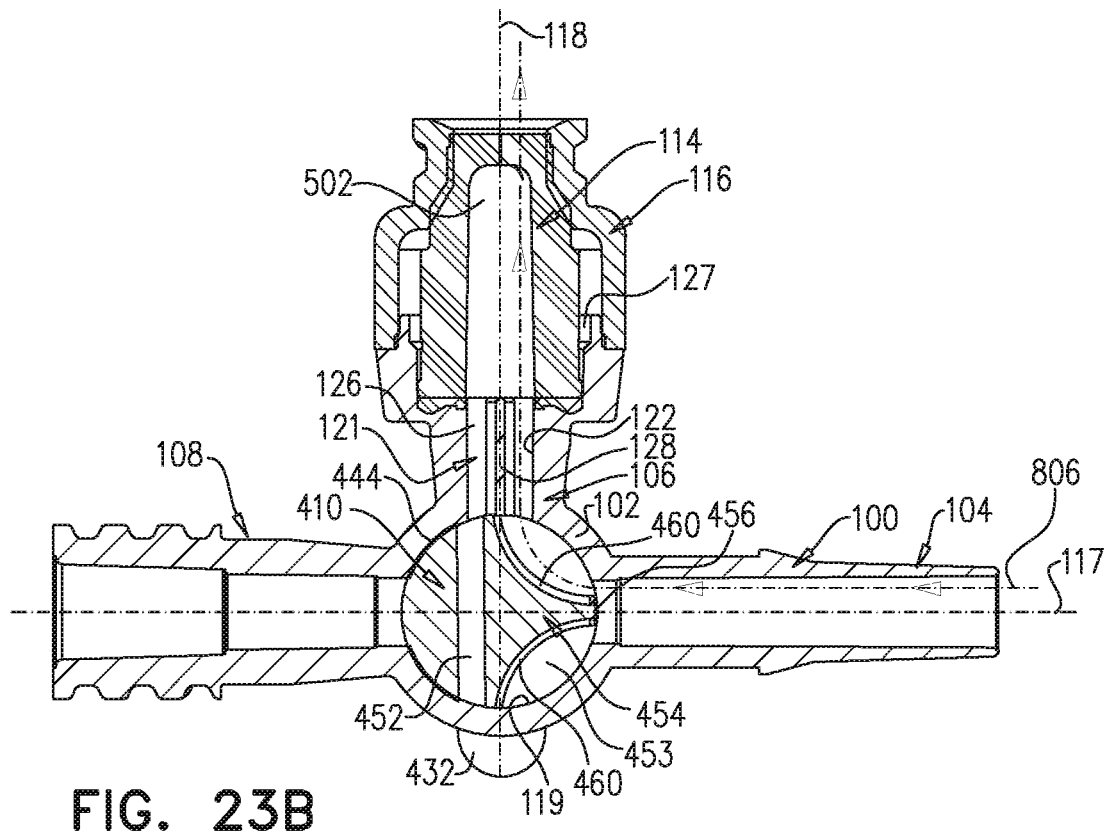

FIGS. 19B and 23B illustrate a second operating position of the stopcock of FIG. 15, where the handle element 410 is rotatably disposed within the main tubular portion 102 of the housing element 100, such that finger engageable protrusion 534 is aligned with port 108 of the housing element 100 and extends along an axis, which is parallel to axis 117.

FIGS. 19B and 23B illustrate a second operating position of the stopcock of FIG. 15, which is typically employed for drawing blood or other fluids from the patient. The user typically connects a syringe to port 106, such that the luer of the syringe penetrates elastomeric element 114, such that the luer of the syringe communicates with an internal volume 502 of the elastomeric element 114, and draws blood from the patient through port 104, via recess 453 as indicated by an arrow 806, through port 106 to the syringe. It is appreciated that this operating position may also be used for supplying a medicament to the patient when port 108 is closed, in a flow direction opposite to that indicated by arrow 806.

It is particularly noted that in this operating position, due to the fact that the side-to-side bore 452 is isolated from the recess 453, the entire fluid flow from port 104 enters the second fluid flow passage, which is preferably defined by the circumferential recess 453, such that in this operating position, the fluid flows along concave wall surface 460 of the fluid flow guide 454, which effectively directs the flow into cylindrical bore 122 of port 106, and further into the internal volume 502 of the elastomeric element 114 and into the syringe, which is connected to port 106. There is no fluid flow through the side-to-side bore 452 in this second operating orientation of the stopcock.

Figure 23C:
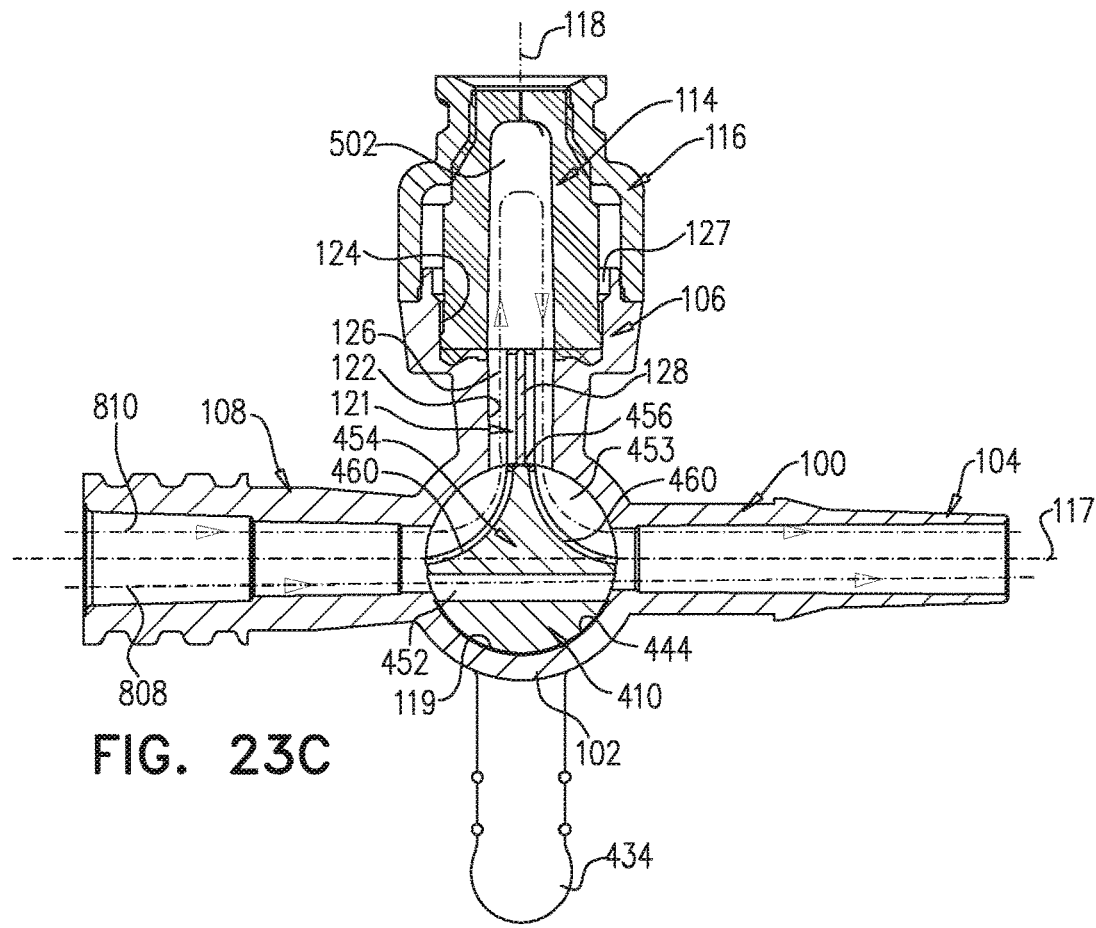

FIGS. 19C and 23C illustrate a third operating position of the stopcock of FIG. 15, where the handle element 410 is rotatably disposed within the main tubular portion 102 of the housing element 100, such that finger engageable protrusion 434 extends in a direction opposite to port 106 of the housing element 100 and extends along an axis, which is parallel to axis 118.

FIGS. 19C and 23C illustrate a third operating position of the stopcock of FIG. 15, which is typically employed for supplying a liquid to the patient from port 108 to port 104. Liquid flows via the first fluid flow passage from port 108 via bore 452 and into port 104, as indicated by an arrow 808. Liquid also simultaneously flows via the second fluid flow passage from port 108 via recess 453, around fluid flow guide 454 into interior volume 121 of port 106 and thereafter around fluid flow guide 128 into internal volume 502 of the elastomeric element 114, thereby flushing residual liquid therefrom, and flowing further around fluid flow guides 128 and 454 into port 104 and to the patient, as indicated by an arrow 810.

It is particularly noted that in this operating position, a portion of fluid from port 108 enters the first fluid flow passage, defined by side-to-side bore 452. This portion of fluid flows entirely along side-to-side bore 452 and into port 104.

It is particularly noted that the remaining portion of the fluid from port 108 enters the second fluid flow passage, which is preferably defined by the circumferential recess 453, such that in this operating position, the fluid flows along the first concave wall surface 460 of the fluid flow guide 454, which effectively directs the entire fluid flow that enters the second fluid flow passage into cylindrical bore 122 of port 106. Further, due to the presence of fluid flow guide 128 within port 106, the fluid is directed along one side of the fluid flow guide 128 into the internal volume 502 of the elastomeric element 114 and while flushing this internal volume, the fluid is directed along the other side of fluid flow guide 128, thereafter along the second concave wall surface 460 of the fluid flow guide 454 and eventually into port 104, as indicated by arrow 810.

It is a particular feature of an embodiment of the present invention that the second fluid flow passage has various configurations in accordance with the configuration of the fluid flow guide 454. When the fluid flows along concave wall surfaces 460 of the fluid flow guide 454, a smooth laminar flow of liquid is provided and singularity points along the fluid flow passage are prevented.

It is a particular feature of an embodiment of the present invention that the flow of liquid from port 108 is bifurcated right upon reaching the main tubular portion 102 of housing element 100, due to the fact that concave wall surface 460 extends along a majority of the longitudinal extent of side-to-side extending bore 452. Specifically, the fact that the concave wall surface 460 extends to the vicinity of the inner facing wall of the central bore 119, causes liquid flowing from port 108 to be bifurcated right upon reaching main tubular element 102 of the housing element 100, thus assuring that a significant portion of liquid from port 108 flows into peripherally-extending recess 453, as indicated by arrow 810, and further into interior volume 121 of port 106 and into internal volume 502 of the elastomeric element 114 in order to provide proper flushing of both the internal volume 502 and of the interior volume 121. It is noted that the remaining portion of liquid from port 108 simultaneously flows through side-to-side extending bore 452, as indicated by arrow 808, in this third operating position of the stopcock in order to increase the flow rate of liquid flowing from port 108 to port 104.

It is a particular feature of the present invention that the provision of fluid flow guides 454 and 128 generally overcomes problems of the presence of residual liquids remaining in the internal volume 121 of port 106 as well as in internal volume 502 of the elastomeric element 114. This is important in various therapeutic situations. For example, when blood is drawn from the patient through port 106, there remains residual blood in the internal volume 121 of port 106 and the internal volume 502 of the elastomeric element 114. This blood, if left in internal volumes 121 and 502 for a period of time, can clot and thus become dangerous if delivered to the patient. In addition, the coagulated blood could occlude the liquid passageway extending through port 106. Various infections could possibly arise as a result of the retained blood.

This feature is also useful when a medicament is supplied to a patient through port 106. If a portion of the medicament remains in the internal volumes 121 of port 106 and 502 of the elastomeric element 114, the dosage of the medicament that the patient receives is less than the intended dosage by an amount which cannot be readily ascertained. In addition, this residual medicament might be inadvertently supplied to the patient during a subsequent use of the stopcock, which could cause harm to the patient.

The present invention provides for automatic flushing of the liquid, such as blood or medicament from the internal volumes 121 and 502 and typically returning it to the patient without requiring the use of extra syringes and the opening of the medical set to the atmosphere, thereby increasing the chance of contamination.

It is an additional particular feature of an embodiment of the present invention that first fluid flow passage through side-to-side bore 452 is provided for increasing the flow rate through the stopcock of FIG. 15 while maintaining the flushing feature of volumes 121 and 502 via the second fluid flow passage.

Figure 23D:
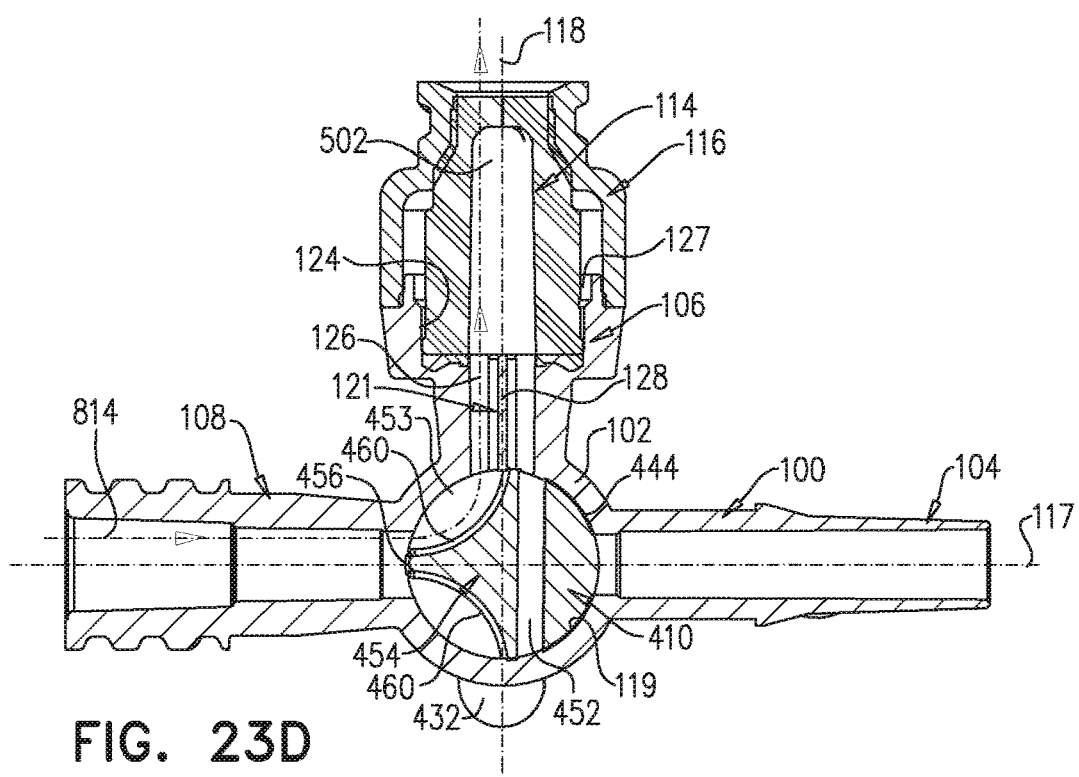

FIGS. 19D and 23D illustrate a fourth operating position of the stopcock of FIG. 15, where the handle element 410 is rotatably disposed within the main tubular portion 102 of the housing element 100, such that finger engageable protrusion 434 is aligned with port 104 of the housing element 100 and extends along an axis, which is parallel to axis 117.

FIGS. 19D and 23D illustrate a fourth operating position of the stopcock of FIG. 15, which may be used for flushing the IV set upstream of the stopcock, when port 106 is open to the atmosphere as by insertion of a male luer connector, such as a syringe tip (not shown), into the elastomeric element 114 of the valve thereof. The insertion of the male luer connector activates the flow of liquid from port 108 via the second fluid flow passage through recess 453, around fluid flow guide 354 into interior volume 121 of port 106 and thereafter around fluid flow guide 128 into internal volume 502 of the elastomeric element 114, flushing residual liquid therefrom, via port 106 to the IV line, as indicated by an arrow 814.

It is particularly noted that in this operating position, due to the fact that the side-to-side bore 452 is isolated from the recess 453, the entire amount of fluid from port 108 enters the second fluid flow passage, which is preferably defined by the circumferential recess 453, such that in this operating position, the fluid flows along concave wall surface 460 of the fluid flow guide 454, which effectively directs the flow into cylindrical bore 122 of port 106, and further into the internal volume 502 of the elastomeric element 114 and into the syringe, which is connected to port 106.

It is a particular feature of an embodiment of the present invention that the second fluid flow passage has various configurations in accordance with the configuration of the fluid flow guide 454. When the fluid flows along concave wall surface 460 of the fluid flow guide 454, a smooth laminar flow of liquid is provided and singularity points along the fluid flow passage are prevented.

Alternatively, this operating position may be employed for pushing liquid via the side port 106, through port 108, in a direction opposite arrow 814, for uses such as mixing liquid in the pressure bag.

It is appreciated that the stopcock in accordance with embodiments of the present invention illustrated in FIGS. 1-23D is operable is an arterial monitoring set. The arterial monitoring set generally includes a fluid-filled bag and a tube portion leading to a patient's artery. An arterial pressure sensor is coupled in a series along the tube portion and provides a visible output on a conventional monitor. Downstream of arterial pressure sensor there is provided the stopcock of the type described hereinabove with reference to any of FIGS. 1-23D, including a swabbable valve having an elastomeric element 114.

Stopcock such as shown and illustrated in FIGS. 19A, 20A, 21A, 22A and 23A is preferably used for transferring liquid through an arterial set, including the stopcock, from the bag to the artery of the patient.

Stopcock such as shown and illustrated in FIGS. 19B, 20B, 21B, 22B and 23B, is typically employed for drawing blood or other fluids from the patient, by employing a syringe coupled to the swabbable valve. It is appreciated that this operating position may also be used for supplying medicament to the patient via syringe.

Stopcock such as shown and illustrated in FIGS. 19C, 20C, 21C, 22C and 23C, is typically employed for supplying a liquid to the patient from the arterial set. Liquid flows through the stopcock and flushes the internal volume of the swabbable valve and of the port in which it is located, flushing residual liquid therefrom to the patient.

Stopcock such as shown and illustrated in FIGS. 19D, 20D, 21D, 22D and 23D, is typically employed for flushing the IV set upstream of the stopcock, when port 106 is open to the atmosphere as by insertion of a male luer connector, such as a syringe tip (not shown), into the elastomeric element 114 of the valve thereof.

Because it enables an operator to easily draw blood without exposing the arterial line to the atmosphere, use of a stopcock shown in any of FIGS. 1-23D in a monitoring set reduces both the risk of contamination and the need for extra covers or plugs and provides for both flushing of the internal volume of the stopcock and the internal volume of the valve and for increasing the fluid flow rate through the stopcock.

For routine use in arterial lines, the stopcock is employed in a position such as that shown in FIG. 19A and any of FIG. 20A, 21A, 22A or 22A, where the fluid flows from the arterial line to the patient without making contact with the elastomeric element 114 of the valve.

To draw blood from the patient, the operator places the handle of the stopcock in the operative orientation shown in FIG. 19B and any of FIG. 20B, 21B, 22B or 23B, introduces a syringe to the valve, thereby opening it, and draws blood.

After blood is drawn, residual blood remains in the internal volumes of the valve and the side port of the stopcock. This residual blood, if not removed from the stopcock, may cause damage to the patient as discussed hereinabove with reference to FIG. 19C and any of FIGS. 20C, 21C, 22C and 23C.

In order to clear the residual blood from the internal volumes, the operator places the handle of the stopcock in the operative orientation shown in FIG. 19C and any of FIGS. 20C, 21C, 22C and 23C. In this orientation, the flow of liquid in the arterial line flushes the internal volumes of both the valve and the side port of the stopcock and clears the residual blood therefrom.

For use of the stopcock in monitoring the arterial blood pressure of the patient, the flow of liquid must not come in contact with the electromeric component of the valve. Therefore, when the operator has removed the residual blood from the internal volumes of the valve and the side port of the stopcock, he would again place the handle of the stopcock in the operative orientations seen in FIG. 19A and any of FIG. 20A, 21A, 22A or 22B.

It is appreciated that the stopcock structure shown and described hereinabove may have many advantageous uses in addition to those described specifically hereinabove.

It will be appreciated by persons skilled in the art that the present invention is not limited to what has been particularly shown and described hereinabove. Rather the scope of the present invention includes both combinations and subcombinations of the various features described hereinabove as well as modifications and variations thereof as would occur to a person of skill in the art upon reading the foregoing specification and which are not in the prior art.

The invention claimed is:

1. A stopcock comprising:
   a housing element defining a central bore and at least first, second and third ports; and
   a handle element which is selectably positionable relative to said housing element, said handle element has a partially peripherally-extending recess;
   at least one of said housing element and said handle element defining:
   a first fluid flow passageway communicating between two of said at least first, second and third ports;
   a second fluid flow passageway communicating between at least two of said at least first, second and third ports, wherein both said first fluid flow passageway and said second fluid flow passageway are defined by a shaft portion of said handle element;
   wherein said first fluid flow passageway is defined by at least one side-to-side extending bore formed within said shaft portion of said handle element; and
   a first fluid flow guide associated with said second fluid flow passageway, said first fluid flow guide extending radially towards an inner facing wall of said central bore and partially bifurcating said partially peripherally-extending recess; and
   a second fluid flow guide extending radially and partially bifurcating one of said at least one of the first, second and third ports, said second fluid flow guide being associated with at least one of said first fluid flow passageway and said second fluid flow passageway.

2. The stopcock according to claim 1 and wherein said second fluid flow passageway being configured for enabling flushing an internal volume of at least one of said first, second and third ports by a fluid flow which does not flow entirely through said port whose internal volume is being flushed, and
said first fluid flow passageway being configured for increasing a fluid flow rate between two of said at least first, second and third ports.

3. The stopcock according to claim 1 and wherein said first fluid flow guide partially bifurcates said second fluid flow passageway.

4. The stopcock according to claim 1 and wherein said first fluid flow guide comprising an outward facing edge which sealingly engages said inner facing wall of said central bore, and when said outward facing edge of said first fluid flow guide is not located opposite any of said first, second and third ports, flow of liquid through said second fluid flow passageway is prevented and flow of liquid through said first fluid flow passageway is allowed.

5. The stopcock according to claim 1 and wherein said first fluid flow guide comprising an outward facing edge which is slightly spaced from said inner facing wall of said central bore, and when said outward facing edge of said first fluid flow guide is not located opposite any of said first, second and third ports, minimal flow of liquid through said second fluid flow passageway is allowed and flow of liquid through said first fluid flow passageway is allowed.

6. The stopcock according to claim 1 and wherein said handle element and said housing element being arrangeable in multiple mutual positions.

7. The stopcock according to claim 6 and wherein said first fluid flow guide and said second fluid flow passageway being configured for enabling flushing an internal volume of at least one of said first, second and third ports by a fluid flow which does not flow entirely through said port whose internal volume is being flushed when said housing element and said handle element are in at least one of said multiple mutual positions.

8. The stopcock according to claim 6 and wherein said first fluid flow passageway and said second fluid flow passageway are operative simultaneously in at least one of said multiple mutual positions.

9. The stopcock according to claim 1 and wherein said at least one side-to-side extending bore is spaced from said recess.

10. The stopcock according to claim 1 and wherein said at least one side-to-side extending bore is interconnected with said recess.

11. The stopcock according to claim 6 and wherein said first fluid flow passageway is fluidly connected with said second fluid flow passageway in at least one of said mutual positions.

12. The stopcock according to claim 6 and wherein said first fluid flow passageway is fluidly isolated from said second fluid flow passageway in at least one of said mutual positions.

13. A stopcock comprising:
a housing element defining a central bore and at least first, second and third ports, and
a handle element, which is selectably positionable relative to said housing element, said handle element has a partially peripherally-extending recess;
said housing element and said handle element being arrangeable in multiple mutual positions,
at least one of said housing element and said handle element defining a first fluid flow passageway communicating between two of said at least first, second and third ports, and a second fluid flow passageway communicating between at least two of said at least first, second and third ports, selection of said ports being in accordance with a relative position of said handle element relative to said housing element;
said first fluid flow passageway including a side-to-side extending bore extending through said handle, and said second fluid flow passageway including a first fluid flow guide extending radially towards an inner facing wall of said central bore and partially bifurcating said partially peripherally-extending recess, and
a second fluid flow guide extending radially and partially bifurcating one of said at least one of the first, second and third ports, said second fluid flow guide being associated with at least one of said first fluid flow passageway and said second fluid flow passageway.

14. The stopcock according to claim 13 and wherein said first fluid flow passageway and said second fluid flow passageway are operative simultaneously in at least one of said multiple mutual positions.

15. The stopcock according to claim 13 and wherein said second fluid flow passageway being configured for enabling flushing an internal volume of at least one of said first, second and third ports by a fluid flow which does not flow entirely through said port whose internal volume is being flushed, and
said first fluid flow passageway being configured for increasing a fluid flow rate between two of said at least first, second and third ports.

16. The stopcock according to claim 13 and wherein said first fluid flow guide comprising an outward facing edge which sealingly engages an inner facing wall of said central bore, and when said outward facing edge of said first fluid flow guide is not located opposite any of said first, second and third ports, flow of liquid through said second fluid flow passageway is prevented and flow of liquid through said first fluid flow passageway is allowed.

17. The stopcock according to claim 13 and wherein said first fluid flow guide comprising an outward facing edge which is slightly spaced from an inner facing wall of said central bore, and when said outward facing edge of said first fluid flow guide is not located opposite any of said first, second and third ports, minimal flow of liquid through said second fluid flow passageway is allowed and flow of liquid through said first fluid flow passageway is allowed.

* * * * *